(12) United States Patent
Maleki

(10) Patent No.: US 8,761,603 B1
(45) Date of Patent: Jun. 24, 2014

(54) DYNAMICALLY RECONFIGURABLE SENSOR ARRAYS

(75) Inventor: Lute Maleki, Pasadena, CA (US)

(73) Assignee: OEwaves, Inc., Pasadena, CA (US)

( * ) Notice: Subject to any disclaimer, the term of this patent is extended or adjusted under 35 U.S.C. 154(b) by 1030 days.

(21) Appl. No.: 12/713,108

(22) Filed: Feb. 25, 2010

Related U.S. Application Data

(60) Provisional application No. 61/155,450, filed on Feb. 25, 2009.

(51) Int. Cl.
*H04B 10/00* (2013.01)

(52) U.S. Cl.
USPC .......................................... 398/129

(58) Field of Classification Search
USPC .......................... 398/122, 127, 129
See application file for complete search history.

(56) References Cited

U.S. PATENT DOCUMENTS

| | | | |
|---|---|---|---|
| 5,204,640 A | 4/1993 | Logan | |
| 5,220,292 A | 6/1993 | Bianchini et al. | |
| 5,723,856 A | 3/1998 | Yao et al. | |
| 5,751,747 A | 5/1998 | Lutes et al. | |
| 5,777,778 A | 7/1998 | Yao | |
| 5,917,179 A | 6/1999 | Yao | |
| 5,929,430 A | 7/1999 | Yao et al. | |
| 5,985,166 A | 11/1999 | Unger et al. | |
| 6,080,586 A | 6/2000 | Baldeschwieler et al. | |
| 6,178,036 B1 | 1/2001 | Yao | |
| 6,203,660 B1 | 3/2001 | Unger et al. | |
| 6,389,197 B1 | 5/2002 | Iltchenko et al. | |
| 6,417,957 B1 | 7/2002 | Yao | |
| 6,473,218 B1 | 10/2002 | Maleki et al. | |
| 6,476,959 B2 | 11/2002 | Yao | |
| 6,487,233 B2 | 11/2002 | Maleki et al. | |
| 6,488,861 B2 | 12/2002 | Iltchenko et al. | |
| 6,490,039 B2 | 12/2002 | Maleki et al. | |
| 6,535,328 B2 | 3/2003 | Yao | |
| 6,567,436 B1 | 5/2003 | Yao et al. | |
| 6,570,692 B2* | 5/2003 | Doucet et al. | 398/121 |
| 6,580,532 B1 | 6/2003 | Yao et al. | |
| 6,594,061 B2 | 7/2003 | Huang et al. | |
| 6,762,869 B2 | 7/2004 | Maleki et al. | |
| 6,795,481 B2 | 9/2004 | Maleki et al. | |
| 6,798,947 B2 | 9/2004 | Iltchenko | |
| 6,853,479 B1 | 2/2005 | Ilchenko et al. | |
| 6,871,025 B2 | 3/2005 | Maleki et al. | |
| 6,873,631 B2 | 3/2005 | Yao et al. | |

(Continued)

FOREIGN PATENT DOCUMENTS

| | | |
|---|---|---|
| WO | WO0196936 A1 | 12/2001 |
| WO | WO2005038513 A2 | 4/2005 |

(Continued)

OTHER PUBLICATIONS

Bernstein, N.P., et al., "Reconfigurable Photonic-Based RF and Data Signal Distribution Systems for Space Based Sensor and Avionics Applications," SPIE Proceedings Photonics for Space Environments V, vol. 3124, pp. 78-83, Oct. 1997.

(Continued)

*Primary Examiner* — Danny Leung
(74) *Attorney, Agent, or Firm* — Perkins Coie LLP

(57) ABSTRACT

Examples and implementations of reconfigurable sensors in a sensor array for performing various reconfigurable sensing functions.

20 Claims, 14 Drawing Sheets

(56) References Cited

U.S. PATENT DOCUMENTS

| | | |
|---|---|---|
| 6,879,752 B1 | 4/2005 | Ilchenko et al. |
| 6,901,189 B1 | 5/2005 | Savchenkov et al. |
| 6,906,309 B2 | 6/2005 | Sayyah et al. |
| 6,922,497 B1 | 7/2005 | Savchenkov et al. |
| 6,928,091 B1 | 8/2005 | Maleki et al. |
| 6,943,934 B1 | 9/2005 | Ilchenko et al. |
| 6,987,914 B2 | 1/2006 | Savchenkov et al. |
| 7,024,069 B2 | 4/2006 | Savchenkov et al. |
| 7,043,117 B2 | 5/2006 | Matsko et al. |
| 7,050,212 B2 | 5/2006 | Matsko et al. |
| 7,061,335 B2 | 6/2006 | Maleki et al. |
| 7,062,131 B2 | 6/2006 | Ilchenko |
| 7,092,591 B2 | 8/2006 | Savchenkov et al. |
| 7,133,180 B2 | 11/2006 | Ilchenko et al. |
| 7,173,749 B2 | 2/2007 | Maleki et al. |
| 7,184,451 B2 | 2/2007 | Ilchenko et al. |
| 7,187,870 B2 | 3/2007 | Ilchenko et al. |
| 7,218,662 B1 | 5/2007 | Ilchenko et al. |
| 7,248,763 B1 | 7/2007 | Kossakovski et al. |
| 7,260,279 B2 | 8/2007 | Gunn et al. |
| 7,283,707 B1 | 10/2007 | Maleki et al. |
| 7,356,214 B2 | 4/2008 | Ilchenko |
| 7,362,927 B1 | 4/2008 | Ilchenko et al. |
| 7,369,722 B2 | 5/2008 | Yilmaz et al. |
| 7,379,672 B2 * | 5/2008 | Wang et al. .................. 398/115 |
| 7,389,053 B1 | 6/2008 | Ilchenko et al. |
| 7,400,796 B1 | 7/2008 | Kossakovski et al. |
| 7,440,651 B1 | 10/2008 | Savchenkov et al. |
| 7,460,746 B2 | 12/2008 | Maleki et al. |
| 7,480,425 B2 | 1/2009 | Gunn et al. |
| 7,518,374 B1 | 4/2009 | Olsson et al. |
| 7,587,144 B2 | 9/2009 | Ilchenko et al. |
| 7,630,417 B1 | 12/2009 | Maleki et al. |
| 7,634,201 B2 | 12/2009 | Maleki et al. |
| 8,139,945 B1 * | 3/2012 | Amir et al. .................. 398/126 |
| 2001/0038651 A1 | 11/2001 | Maleki et al. |
| 2002/0018611 A1 | 2/2002 | Maleki et al. |
| 2002/0018617 A1 | 2/2002 | Iltchenko et al. |
| 2002/0021765 A1 | 2/2002 | Maleki et al. |
| 2002/0081055 A1 | 6/2002 | Painter et al. |
| 2002/0085266 A1 | 7/2002 | Yao |
| 2002/0097401 A1 | 7/2002 | Maleki et al. |
| 2003/0160148 A1 | 8/2003 | Yao et al. |
| 2004/0100675 A1 | 5/2004 | Matsko et al. |
| 2004/0109217 A1 | 6/2004 | Maleki et al. |
| 2004/0218880 A1 | 11/2004 | Matsko et al. |
| 2004/0240781 A1 | 12/2004 | Savchenkov et al. |
| 2005/0017816 A1 | 1/2005 | Ilchenko et al. |
| 2005/0063034 A1 | 3/2005 | Maleki et al. |
| 2005/0074200 A1 | 4/2005 | Savchenkov et al. |
| 2005/0123306 A1 | 6/2005 | Ilchenko et al. |
| 2005/0128566 A1 | 6/2005 | Savchenkov et al. |
| 2005/0175358 A1 | 8/2005 | Ilchenko et al. |
| 2005/0248823 A1 | 11/2005 | Maleki et al. |
| 2005/0286907 A1 * | 12/2005 | Masuda et al. ................. 398/186 |
| 2007/0009205 A1 | 1/2007 | Maleki et al. |
| 2007/0153289 A1 | 7/2007 | Yilmaz et al. |
| 2008/0001062 A1 | 1/2008 | Gunn et al. |
| 2008/0075464 A1 | 3/2008 | Maleki et al. |
| 2008/0310463 A1 | 12/2008 | Maleki et al. |
| 2009/0097516 A1 | 4/2009 | Maleki et al. |
| 2009/0135860 A1 | 5/2009 | Maleki et al. |
| 2009/0208205 A1 | 8/2009 | Eliyahu et al. |
| 2009/0251705 A1 | 10/2009 | Le et al. |
| 2009/0310629 A1 | 12/2009 | Maleki et al. |
| 2009/0324251 A1 | 12/2009 | Ilchenko et al. |

FOREIGN PATENT DOCUMENTS

| | | |
|---|---|---|
| WO | WO2005055412 A2 | 6/2005 |
| WO | WO2005067690 A2 | 7/2005 |
| WO | WO2005122346 A2 | 12/2005 |
| WO | WO2006076585 A2 | 7/2006 |
| WO | WO2007143627 A2 | 12/2007 |

OTHER PUBLICATIONS

Braginsky, V.B., et al., "Quality-Factor and Nonlinear Properties of Optical Whispering-Gallery Modes," Physics Letters A, 137(7, 8):393-397, May 1989.

Chalivendra, G., et al., "FPGA Based Re-Configurable Wireless Sensor Network Protocol," 2008 International Conference on Electronic Design, pp. 1-4, Dec. 2008.

Eliyahu, D., et al., "Low Phase Noise and Spurious Levels in Multi-Loop Opto-Electronic Oscillators," Proceedings of the 2003 IEEE International Frequency Control Sympsoium and PDA Exhibition, pp. 405-410, May 2003.

Eliyahu, D., et al., "Modulation Response (S21) of the Coupled Opto-Electronic Oscillator," Proceedings of the 2005 IEEE International Frequency Control Symposium and Exposition, pp. 850-856, Aug. 2005.

Eliyahu, D., et al., "Tunable, Ultra-Low Phase Noise YIG Based Opto-Electronic Oscillator," IEEE MTT-S International Microwave Symposium Digest, 3:2185-2187, Jun. 2003.

Gorodetsky, M.L., et al., "Optical Microsphere Resonators: Optimal Coupling to High-Q Whispering-Gallery Modes," J. Opt. Soc. Am. B, 16(1):147-154, Jan. 1999.

Gorodetsky, M.L., et al., "Rayleigh Scattering in High-Q Microspheres," J. Opt. Soc. Am. B, 17(6):1051-1057, Jun. 2000.

Gorodetsky, M.L., et al., "Ultimate Q of Optical Microsphere Resonators," Optics Letters, 21(7):453-455, Apr. 1996.

Hryniewicz, J.V., et al., "Higher Order Filter Response in Coupled Microring Resonators," IEEE Photonics Technology Letters, 12(3):320-322, Mar. 2000.

Huang, S., et al., "A 'Turnkey' Optoelectronic Oscillator with Low Acceleration Sensitivity," 2000 IEEE/EIA International Frequency Control Symposium and Exhibition, pp. 269-279, Jun. 2000.

Ilchenko, V., et al., "Electronically Tunable Photonic Microresonators and Photonic Bandgap Waveguide Coupling for Micro-Optoelectronic Oscillators," GOMACTech 2003, Tampa, Florida, pp. 1-4.

Ilchenko, V., et al., "High-Q Microsphere Cavity for Laser Stabilization and Optoelectronic Microwave Oscillator," Proceedings SPIE Microresonators and Whispering-Gallery Modes, vol. 3611, pp. 190-198, Jan. 1999.

Ilchenko, V., et al., "Microsphere Integration in Active and Passive Photonics Devices," Proc. of SPIE Laser Resonators III, vol. 3930, pp. 154-162, Jan. 2000.

Ilchenko, V., et al., "Microtorus: A High-Finesse Microcavity with Whispering-Gallery Modes," Optics Letters, 26 (5):256-258, Mar. 2001.

Ilchenko, V., et al., "Pigtailing the High-Q Microsphere Cavity: A Simple Fiber Coupler for Optical Whispering-Gallery Modes," Optics Letters, 24(11):723-725, Jun. 1999.

Ilchenko, V., et al., "Sub-Micro Watt Photonic Microwave Receiver," IEEE Photonics Technology Letters, 14 (11):1602-1604, Nov. 2002.

Ilchenko, V., et al., "Tunability and Synthetic Lineshapes in High-Q Optical Whispering Gallery Modes," Proc. of SPIE Laser Resonators and Beam Control VI, vol. 4969, pp. 195-206, Jan. 2003.

Ilchenko, V., et al., "Whispering-Gallery-Mode Electro-Optic Modulator and Photonic Microwave Receiver," J. Opt. Soc. Am. B, 20(2):333-342, Feb. 2003.

Ito, H., et al., "InP/InGaAs Uni-Travelling-Carrier Photodiode with 310 GHz Bandwidth," Electronics Letters, 36 (21):1809-1810, Oct. 2000.

Logan, R., et al., "Stabilization of Oscillator Phase Using a Fiber-Optic Delay-Line," IEEE 45th Annual Symposium on Frequency Control, pp. 508-512, May 1991.

Maleki, L., "The Opto-Electronic Oscillator: Prospects for Extending the State of the Art in Reference Frequency Generation," International Topical Meeting on Microwave Photonics, pp. 195-198, Oct. 1998.

Matsko, A., et al., "Active Mode Locking with Whispering-Gallery Modes," J. Opt. Soc. Am. B, 20(11):2292-2296, Nov. 2003.

Matsko, A., et al., "Whispering-Gallery-Mode based Optoelectronic Microwave Oscillator," Journal of Modern Optics, 50(15-17):2523-2542, Feb. 2004.

(56) References Cited

OTHER PUBLICATIONS

Matsko, A., et al., "Whispering-Gallery-Mode Resonators as Frequency References. I. Fundamental Limitations," J. Opt. Soc. Am. B, 24(6):1324-1335, Jun. 2007.

Myers, L.E., et al., "Quasi-Phase-Matched Optical Parametric Oscillators in Bulk Periodically Poled LiNbO3," J. Opt. Soc. Am. B, 12(11):2102-2116, Nov. 1995.

Savchenkov, A., et al., "RF photonic signal processing components: From high order tunable filters to high stability tunable oscillators," IEEE Radar Conference, pp. 1-6, May 2009.

Savchenkov, A., et al., "Tunable Resonant Single-Sideband Electro-Optical Modulator," Digest of the IEEE/LEOS Summer Topical Meetings, pp. 63-64, Jul. 2009.

Savchenkov, A., et al., "Whispering-Gallery-Mode Resonators as Frequency References. II. Stabilization," J. Opt. Soc. Am. B, 24(12): 2988-2997, Dec. 2007.

Vassiliev, V.V., et al., "Narrow-Line-Width Diode Laser with a High-Q Microsphere Resonator," Optics Communications, 158(1-6):305-312, Dec. 1998.

Yao, X.S., et al., "A Novel Photonic Oscillator," Digest of the LEOS Summer Topical Meetings, pp. 17-18, Aug. 1995.

Yao, X.S., et al., "A Novel Photonic Oscillator," TDA Progress Report 42-122, pp. 32-43, Aug. 1995.

Yao, X.S., et al., "Converting Light into Spectrally Pure Microwave Oscillation," Optics Letters, 21(7):483-485, Apr. 1996.

Yao, X.S., et al., "Coupled Optoelectronic Oscillators for Generating Both RF Signal and Optical Pulses," Journal of Lightwave Tecnhology, 18(1):73-78, Jan. 2000.

Yao, X.S., et al., "Dual Microwave and Optical Oscillator," Optics Letters, 22(24):1867-1869, Dec. 1997.

Yao, X.S., et al., "Multiloop Optoelectronic Oscillator," IEEE Journal of Quantum Electronics, 36(1):79-84, Jan. 2000.

Yao, X.S., et al., "Optoelectronic Microwave Oscillator," J. Opt. Soc. Am. B, 13(8):1725-1735, Aug. 1996.

Yao, X.S., et al., "Optoelectronic Oscillator for Photonic Systems," IEEE Journal of Quantum Electronics, 32 (7):1141-1149, Jul. 1996.

Yu, J., et al., "Compact Optoelectronic Oscillator with Ultra-Low Phase Noise Performance," Electronics Letters, 35 (18):1554-1555, Sep. 1999.

\* cited by examiner

Optical Spectrum of Modulated Optical Beam 1132

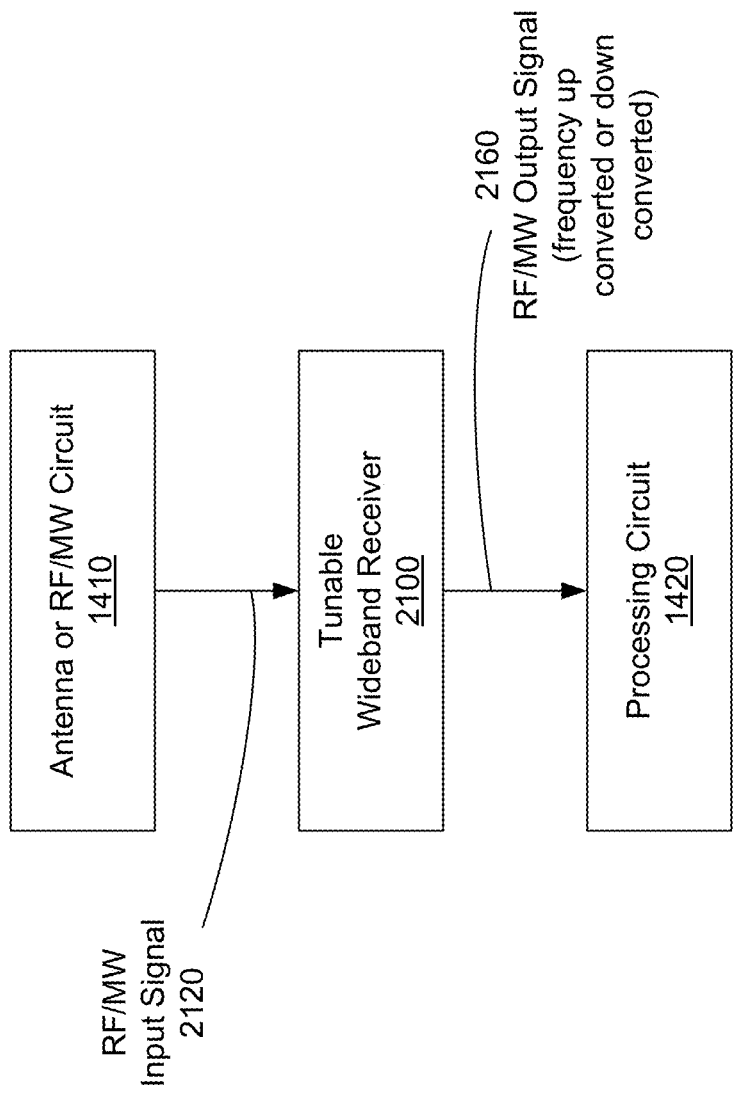

DYNAMICALLY RECONFIGURABLE SENSOR ARRAYS

PRIORITY

This patent document claims priority of U.S. Provisional Application No. 61/155,450 entitled "DYNAMICALLY RECONFIGURABLE SENSOR ARRAYS" and filed on Feb. 25, 2009, the entire disclosure of which is incorporated by reference as part of this document.

BACKGROUND

This document relates to sensors and sensor arrays.

Sensors are devices that receive signals and detect one or more parameters in a received signal from one or more targets of interest. For example, a sensor can be an optical sensor that receives and detects an optical signal for optical imaging, or a radio frequency (RF) sensor that receives and detects a signal at a frequency within the RF spectral band. Some sensors are tunable in frequency and can tune their operating frequency within a spectral range. A sensor can be configured to transmit a signal in addition to receiving a signal and such a sensor is a transceiver.

SUMMARY

Examples and implementations of reconfigurable sensors in a sensor array for performing various reconfigurable sensing functions are provided. In one implementation, a sensor array can include reconfigurable sensors spatially distributed at different locations, where each sensor is adjustable or reconfigurable to change one or more aspects of the sensor operation, and each sensor includes a transceiver in wireless communication with other sensors in the sensor array. The sensors are operable to collaborate with one another via wireless inter-sensor communications to reconfigure one or more aspects of the sensor array.

In another implementation, a method is provided for operating a sensor array of sensors for sensing a target object. This method includes operating a sensor array of reconfigurable sensors that are spatially distributed at different locations with respect to a target object to obtain measurements of the target object; operating the sensors to be in wireless communication with one another in the sensor array; and adjusting either positions of the sensors relative to one another or with respect to the target object to change an aperture of the sensor array in receiving information from the target object to obtain measurements of the target object at different apertures, or/and a frequency of a signal that is received by each sensor from the target object to obtain measurements of the target object at different frequencies.

In yet another implementation, a sensor array is provided to include reconfigurable sensors that are spatially distributed at different locations with respect to a target object, wirelessly communicate with one another within the sensor array, and collaborate with one another via wireless inter-sensor communications to reconfigure one or more aspects of the sensor array in measuring the target object. Each sensor includes a tunable RF sensor that includes an internal photonic module that uses photonic or optical components to process light that is modulated to carry an RF signal to tune a frequency of a received RF signal at the tunable RF sensor from the target object, and a sensor platform vehicle that controls position, orientation and/or motion of each sensor in adjusting an aperture of the sensor array with respect to the target object in receiving signals from the target object.

These and other implementations are described in greater detail in the drawings, the description and the claims.

BRIEF DESCRIPTION OF DRAWINGS

FIG. 14 shows an example of an electronic device that uses the tunable wideband receiver in FIG. 11.

DETAILED DESCRIPTION

Figure 1:
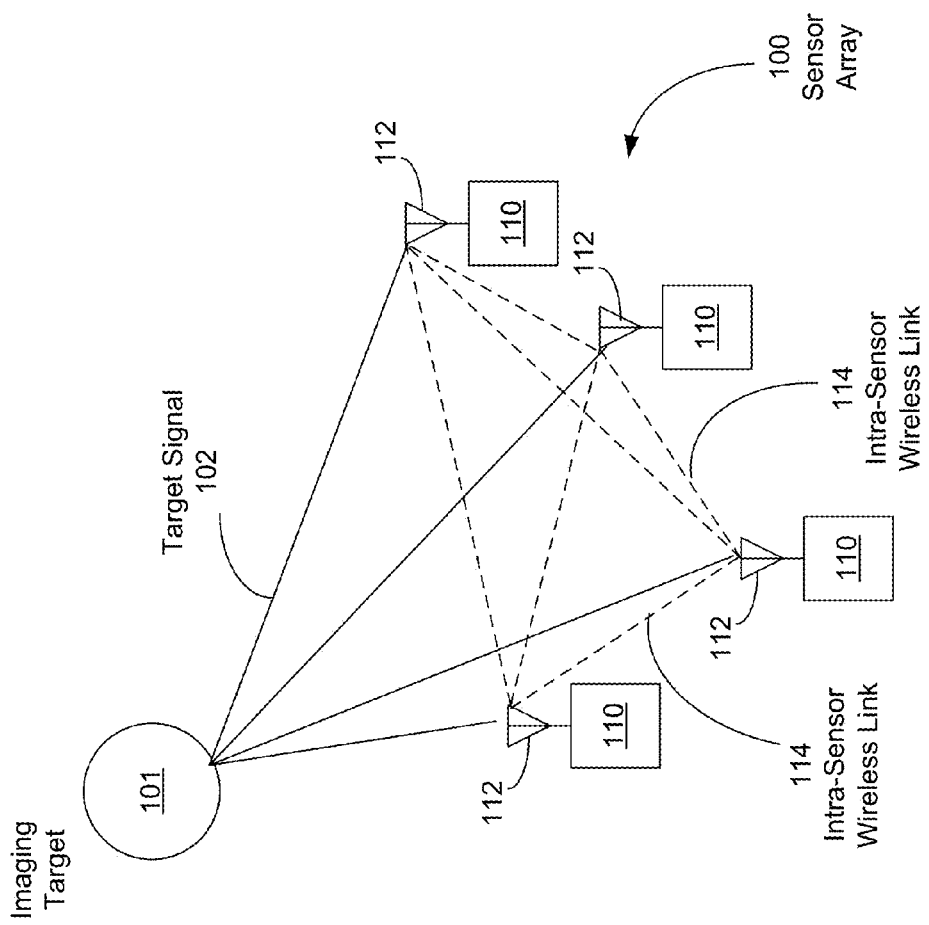
FIG. 1 illustrates an example of a dynamically reconfigurable sensor array formed by sensors that are spatially distributed at different locations.

This document describes dynamically reconfigurable sensor arrays in which one or more aspects of the sensor array operation can be adjusted or reconfigured in response to a change or a need in connection to the sensor array, e.g., a change in the environment of the sensor array, a need for improved detection performance or a change in a target under detection by the sensor array. Such a dynamically reconfigurable sensor array includes multiple physically separated sensors that can be deployed at different locations relative to one another to form the array. Each sensor has a receiver and/or transceiver device and can communicate with other sensors in the array. Notably, each sensor can be adjusted or reconfigured in one or more aspects of the sensor array operation.

Such a reconfigurable sensor array can be implemented as an aggregate array of physically separated sensors that can be dynamically reconfigured in space to provide extended functionality and sensing information beyond what each individual sensor can produce. For example, the reconfigurable aspect of such a sensor array be implemented through one or more of the following: (1) changes or adjustments can be made in parameters of individual sensors in the array, (2) change in the spatial configuration of the individual sensors can be made, (3) the entire array configuration can be adjusted. These adjustments can be used to achieve the desired functionality that would not be easily obtained by individual sensors, or by a fixed array.

In implementations, communications with individual sensors within the sensor array can be performed wirelessly to set the desired parameters, and obtain the needed information. The aggregate information obtained from the sensors can be processed appropriately to represent the output of the sensor array. The individual location of each sensor can be dynamically adjusted in response to changes in the observed target parameters, or for collection of information about various attributes of the target.

This design of the aggregate sensor array is in part based on the recognition that individual physical sensors are limited in their capability and functionality. For example, a single mirror can be a sensor which forms an image of a target with a certain resolution dictated by the optical aperture of the single mirror with respect to the target and the relative position of the single mirror with respect to the target. A collection of multiple mirrors, however, can provide improved imaging resolution from individual images of the target obtained by the mirrors at different locations. Similarly, a multispectral image of a target can be obtained via images at different wavelengths of the radiation that form the images if each mirror in the collection has reflectivity in a particular spectral band. This capability sometimes requires a large structure (such as multi-spectral imagers) to achieve the functionality, and if applied, for example, to a moving target requires that the entire structure be articulated to follow the target. The tunable aspect of the RF receiver on each sensor with the sensor array can be used to obtain RF signals from a target object at a first RF frequency to form a first radar image of the target object and RF signals from the target object at a second, different RF frequency from the target object to obtain a second radar image of the target object. The obtained first radar image and the second radar image can be processed to extract differences in the first and second radar images of the target object.

The aggregate sensor array can be used in an application which involves collection of intelligence data with multiple unmanned platforms where the different sensors are located on the different unmanned platforms. If the data is, for example, radar imaging, the size of the antenna on a unmanned platform determines the resolution of the radar image. If several platforms are dynamically configured appropriately to form a larger, segmented antenna, and the data collected from each is processed accordingly, a higher resolution image can be obtained at the same frequency band. This collection of multiple platforms replaces what would be a much larger platform needed to carry a single radar antenna large enough to achieve the image of the same resolution. Each sensor on a respective unmanned platform can be an RF receiver, such as a photonic RF receiver. In some implementations, such a photonic RF receiver can be configured as a tunable wideband receive capable of receiving signals at multiple bands. Under this design, the collection of multiple platforms form a multiple band radar. Spatial reconfiguration of each platform will produce the antenna of the size appropriate for the particular spectral band. The same ideas apply to imaging at other frequencies, UV to IR, with the appropriate sensors on each platform.

FIG. 1 illustrates an example of such a dynamically reconfigurable sensor array 100 formed by sensors 110 that are spatially distributed at different locations. Each sensor 110 includes a transceiver 112 that transmits one or more transmission signals and receives one or more incoming signals. The transceiver 112 can be operated in the optical, millimeter wave, microwave, or RF spectral range depending on the specific operating requirements for the sensor 110. Each sensor 110 can communicate with one or more other sensors within the array 100 via intra-sensor wireless links 114, which can be wireless signals in the optical, millimeter wave, microwave, or RF spectral range. Each sensor 110 includes a sensor processor that processes information contained in each intra-sensor signal received from another sensor via a respective intra-sensor wireless link 114. Based on the information obtained from one or more other sensors 110, a sensor 110 can respond by adjusting or reconfiguring one or more aspects of the sensor array operation. This adjustment or reconfiguration can be done dynamically during the sensor array operation to render the sensor array 100 to be dynamic, adaptable sensor array rather than a static array.

Each sensor 110 can adjust or reconfigure in various ways. For example, each sensor 110 can adjust its operating frequency for signal transmission or reception from one frequency band to another. As another example, each sensor 110 can adjust its detection sensitivity by increasing or decreasing the amplitude of a received signal. As yet another example, each sensor 110 may be movable by being mounted to a movable sensor vehicle and the position of such a movable sensor can be changed relative to other sensors 110 in the sensor array 100.

Notably, the intra-sensor wireless links 114 allow the sensors 110 in the sensor array 100 to communicate with one another and the sensors 110 can adjust or reconfigure based on the communications with other sensors 110 in a collaborative manner so that the adjustment or reconfiguration by an individual sensor 110 is not independent of other sensors 110 and is part of a collaborative operation of the sensors 110 in the sensor array 100. This combination of (1) individual adjustment or reconfiguration at each sensor 110 and (2) collaborative operations of all sensors 110 within the sensor array 100 provides a partial or complete autonomous nature of the sensor array 100 for a wide range of operations, functions and applications.

Examples for dynamically reconfiguring such a sensor array for multiple functions are described below.

Consider the sensor array 100 of sensors 110 that can be dynamically reconfigured with respect to their spatial distribution so that the sensors 110 can support radar imagery at several frequency bands. Referring to FIG. 1, the sensor array 100 may be an imaging sensor array for imaging a target 101.

The sensors 110 collect target signals 102 at their respective locations. Due to the spatial diversity of the sensors 110 with respect to the imaging target 101, different sensors 110 collect different target signals 102. The detected target signals 102 by the different sensors 110 collectively provide additional information on the image of the target 101 that may not be available in a target signal 102 collected by one or a few sensors 110. The spatially distributed sensors 110 in this example, collectively as an assembly, provide an improved image sensing in a way that is analogous to a synthetic aperture radar to some extent. The sensors 110 may be tuned to operate at different frequencies and to collect images of the target 101 in the different frequencies. One or more sensors 110 may also be moved in their positions to capture images of the target 101 with different sensor spatial arrangements.

In addition, the sensors 110 may also be dynamically reconfigured to function as an array that allows collaboration beyond the sensing function, and into physical arrangements to meet the needs of communications, power, and other infrastructures that support the system.

A specific example of the above reconfigurable sensor array 100 is a swarm of unmanned aerial systems (UAS's), for example, three or more UAV's. Each UAV carries a reconfigurable receiver. Such a reconfigurable receiver can be implemented in various configurations, including tunable photonic receivers described in this document and in U.S. Pat. No. 7,587,144 entitled "Tunable Radio Frequency and Microwave Photonic Filters" and U.S. Pat. No. 7,634,201 entitled "Wideband Receiver Based on Photonics Technology", the disclosures of which are incorporated by reference as part of the disclosure of this document. Each UAV platform carries a conformal antenna in its skin. While each one of these antenna apertures is limited in size to the size of the platform, the swarm might be assembled spatially to synthesize a larger aperture, as in a synthetic aperture radar (SAR) antenna. But then by dynamic reconfiguration, such a system can be used to function as a SAR in L-, S-, X-, Ka- or other bands, as made possible with the wideband receiver technology mentioned above. Furthermore, the swarm may be dynamically reconfigured to accommodate the path of its flight. For example, the spatial configuration of the swarm can be made to conform to a narrow area in an urban environment, or a wide area in the field environment. The concept of dynamically reconfigurable multi-functionality also may be expanded to include autonomous operation, whereby the swarm selects a spatial distribution based on pre-programmed need (e.g., to operate as an x-band system) and based on the results obtained autonomously reconfigures to a different spatial distribution, so that higher resolution images at a different band can be obtained from a desired region of the target area. The example of the SAR imager is for illustration only; other sensing functions including optical imagery are also encompassed by this approach.

In the sensor array 100 in FIG. 1, different sensors 110 can communicate with one another and, based on the information exchanged, collaborate with one another to perform one or more functions. This inter-sensor communications and inter-sensor collaboration may be used to make the sensor array 100 an autonomous system in various applications. In other applications, the sensor array 100 may be configured to wirelessly communicate with an external transceiver that is outside the array 100 to either exchange information with the external transceiver or to carry out a command from the external transceiver. In some implementations, there can be two or more external transceivers.

Figure 2:
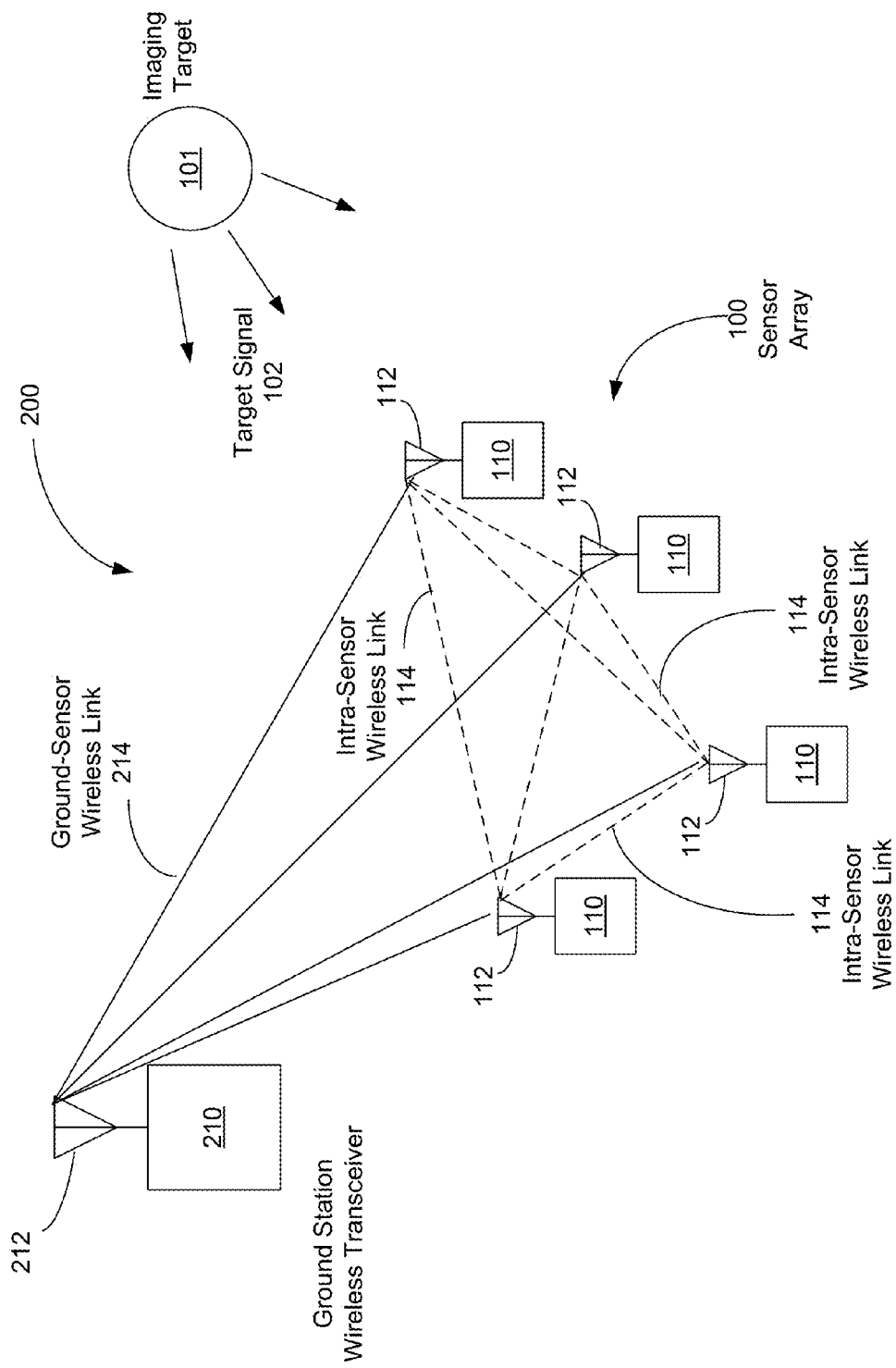
FIG. 2 shows an example of a sensor system where the sensor array wirelessly communicates with a ground station with a wireless transceiver via ground-sensor wireless links.

FIG. 2 shows an example system 200 where the sensor array 100 wirelessly communicates with a ground station 210 with a wireless transceiver 212 via ground-sensor wireless links 214. This wireless communication with an external transceiver can be achieved by using one or more of the sensors 110 in the swarm as the communication hub to the ground, with which other members 110 of the swarm communicate and transfer data as an intra-swarm system. The number of communication hub members may be reconfigurable in turn to accommodate amount of power needed to transfer a large data stream to the ground. Alternatively, the computing and processing of each member can also be dynamically combined to perform "swarm" data processing before the information is transferred to the ground station. This approach allows designing the swarm with distributed infrastructure functionality.

Figure 3:
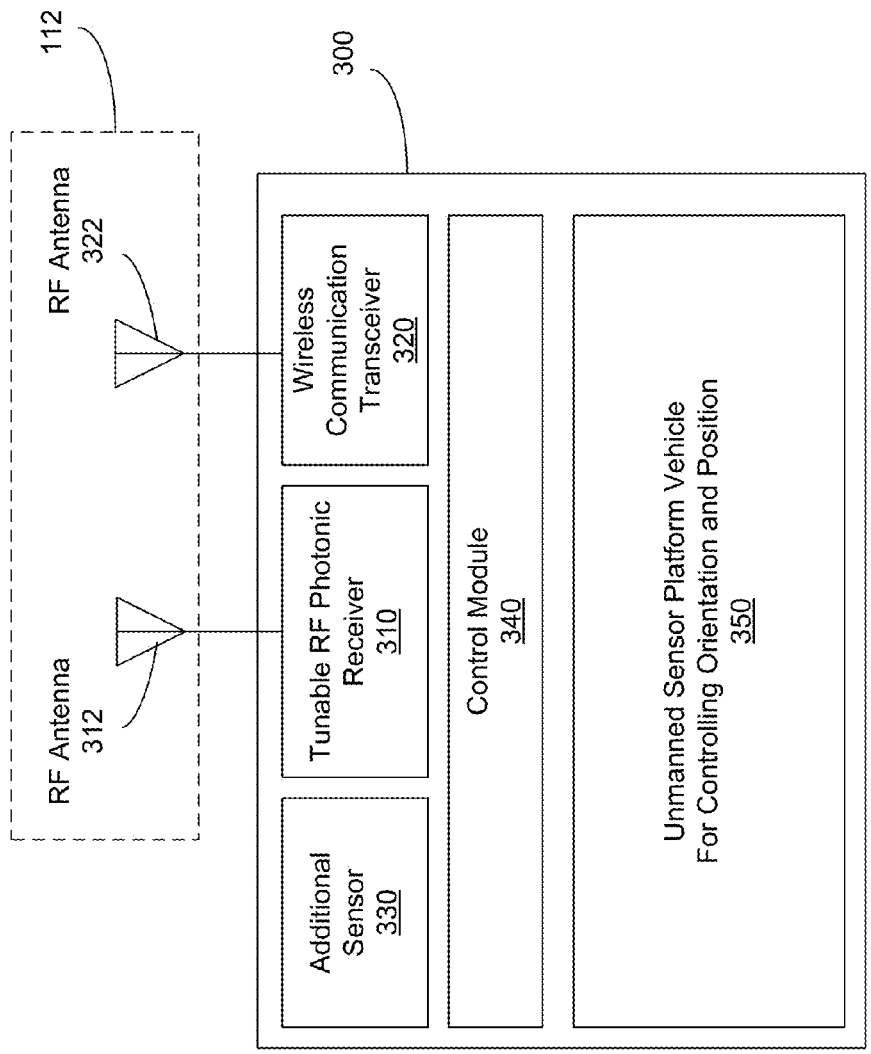
FIG. 3 shows an example of a sensor platform design for the sensor arrays in FIGS. 1 and 2 where the sensor platform includes an unmanned sensor platform vehicle that controls orientation, position or/and motion of the sensor platform to allow for dynamic adjustment of the sensor configuration of the sensor array in the systems in FIGS. 1 and 2.

FIG. 3 shows an example of a sensor platform design 300 for the sensor arrays in FIGS. 1 and 2 where the sensor platform 300 includes an unmanned sensor platform vehicle 350 that controls orientation, position and/or motion of the sensor platform to allow for dynamic adjustment of the sensor configuration of the sensor array in the systems in FIGS. 1 and 2. The unmanned sensor platform vehicle 350 for the sensor platform 300 can be a ground vehicle, a water vessel that either floats on the water or submerges in the water, an airborne vehicle or a space vehicle. In many applications, different sensors may be positioned in the same environment, e.g., all in water, all in the air or space, or all on the ground. Under these circumstances, the unmanned sensor platform vehicles 350 for the sensors in the sensor array may be the same type. In some applications where the sensors of the sensor array are located in different environments, e.g., some in the air while others on the ground, different sensors may be implemented with different types of unmanned sensor platform vehicles 350. Positioning and navigation mechanisms (e.g., GPS) are provided to allow each unmanned sensor platform vehicles 350 to determine its positioning information in nearly real time and thus to control its positioning based on the its current positioning information.

In FIG. 3, the sensor platform 300 includes a tunable RF photonic receiver 310 that allows for tuning of the receiving RF frequency of the receiver 310. This tuning mechanism of the receiver 310 allows for different sensors within the sensor array to operate either at the same receiving frequency for all sensors or at different receiving frequencies for at least some of the sensors and provides various reconfigurable and adaptive sensing possibilities with or without the reconfigurable spatial diversity provided by controlling the orientation, position and/or motion of the sensors with respect to one another and the target. For example, in one sensing configuration, all sensors may be operated at the same receiving frequency in the signal from the target object while changing the spatial configuration of the sensor array to obtain radar images of the target object with different spatial apertures formed by the sensor array in different spatial arrangements at different times. For another example, in a given spatial configuration of the sensor array, the sensors may be operated at the same receiving frequency at the same time to capture the radar image of the target object but are tuned to different receiving frequencies so that radar images of the target object can be captured at different receiving frequencies. For yet another example, both the spatial configuration of the sensor array and the receiving frequency of the sensors can be changed to obtain radar images of the target object at different frequencies for different spatial arrangements of the sensor arrays.

The tunable RF photonic receiver 310 is an RF sensor for obtaining radar images by the respective sensor platform 300. As an option, in some implementations, one or more additional sensors 330 can be implemented to the sensor platform 300, e.g., an optical imaging sensor to obtain optical images. Similar to the RF receiver sensor 310, the operation of an additional sensor 330 for each member of the sensor array can be combined with the reconfigurable spatial arrangements of the sensors relative to one another and with respect to the target object to provide reconfigurable and adaptive sensing operations for the additional sensors 330.

In FIG. 3, a wireless communication transceiver 320 is included in the sensor platform 300 to provide intro-sensor wireless communications as well as communications between the sensors 300 in the systems in FIGS. 1 and 2 and the ground station 210 in FIG. 2. One or more RF antennas 322 can be provided for wireless communication transceiver 320. Referring back to FIGS. 1 and 2, the antennas 312 and 322 collectively correspond to the transceiver antenna 112 in FIGS. 1 and 2. Alternatively, a wireless ground communication transceiver can be implemented to provide the communication with the ground station while a separate wireless intra-sensor communication transceiver can be implemented to provide the intro-sensor communications with other sensors.

The sensor platform 300 uses a control module 340 to control operations of the RF receiver 310, the wireless communication transceiver 320 and any additional sensors 330. With respect to the wireless communication transceiver 320, the control module 340 controls the communications with other sensor platforms within the sensor array and with the ground station in the system in FIG. 2. In addition, the control module 340 controls the unmanned sensor platform vehicle 350 to control the orientation, position and/or motion of the sensor platform 300.

In implementing the sensor array designs in FIGS. 1-3, the tunable RF receiver in each sensor member of the sensor array can be in various configurations. A baseband signal can be carried by a radio frequency (RF) carrier signal to transmit either (1) wirelessly via air or (2) through a cable or waveguide from an RF signal transmitter or generator to an RF signal receiver. In many RF systems, the RF signal receiver can be designed to filter the received RF signal and to mix the filtered RF signal with an RF local oscillator (LO) signal generated by an RF local oscillator to convert the RF signal at the RF carrier frequency to an intermediate frequency (IF) at a lower frequency. The down-converted IF signal is then processed to extract the baseband signal for various signal processing operations. A tunable wideband RF receiver can tune to a range of RF frequencies. Such a wideband RF receiver can be realized using a bank of tunable RF filters to filter the received RF signal to select an RF frequency of interest from the detected input signal of an RF input port or circuit which can be, for example, a wideband RF antenna. A tunable synthesizer can be provided to mix the filtered RF signal output by the bank of tunable RF filters with the RF LO signal to down-convert the RF signal to IF. This approach requires many RF circuit elements, including the bank of filters, synthesizers, mixers, and various stages of signal amplification and thus the wideband receiver can have complex receiver circuitry and suffer losses at various stages in the circuitry. In addition, the frequency tuning range of such RF wideband receivers can be limited and narrow bandwidths can be difficult to achieve in the RF range using RF electronic filter designs.

Tunable wideband receivers in the RF, microwave or millimeter spectral range can be based on photonics technology to use both (1) photonic or optical components and (2) electronic circuit components. Such photonics-based tunable wideband receivers are designed to have electronic input and output interfaces like an all-electronic wideband RF receiver but have an internal photonic module to provide signal processing in the optical domain using the photonic or optical components. For example, in one implementation of a photonics-based wideband receiver, one part of signal processing is performed in the RF, microwave or millimeter domain and another part of the processing is performed in the optical domain. Optical filtering can be performed to select a desired signal component in the received RF, microwave or millimeter signal and tuning of the receiver frequency can also be performed in the optical domain. Signal frequency conversion such as the RF to IF down conversion can also be achieved via optical processing. Such optical processing can be advantageous over electronic processing and can be used to achieve receiver functions or characteristics that may be difficult to achieve using some all-electronic RF, microwave or millimeter wave receivers. Therefore, a tunable RF receiver based on photonic components and processing provide various advantages in implementing the sensor arrays in FIGS. 1-3.

Such tunable photonic RF receives can include RF and microwave filters based on filtering techniques for processing RF and microwave signals by using (1) photonic or optical components and (2) RF and microwave components. In some implementations, a part of the processing is performed in the RF and microwave domain such as applying a microwave or RF input signal to an optical modulator to control optical modulation of light, and another part of the processing is performed in the optical domain such as optical filtering of the modulated light to select one or more desired microwave or RF spectral components as the filtered output. The frequency of a selected spectral component can be tuned by either tuning the frequency of the light that is modulated by the optical modulator or an optical filter that is used to optically filter modulated optical beam.

In one implementation, a device described here includes an input port to receive an input microwave or RF signal, a laser to produce a continuous-wave laser beam, a first optical path to receive a first portion of the laser beam, and a second optical path to receive a second portion of the laser beam. The second optical path includes an optical modulator to modulate the second portion in response to the input signal to produce a modulated optical beam that carries the input signal, and a tunable optical filter to filter the modulated optical beam to select at least one spectral component in the input signal while rejecting other spectral components and to output a filtered modulated optical beam that carries the at least one selected spectral component. The tunable optical filter includes at least two optical resonators that are optically coupled to produce a filter function of at least a second order. A tuning control unit is provided in the device in this implementation to tune at least one of the two optical resonators to change a frequency of the at least one selected spectral component. In addition, an optical detector is provided to combine the first portion from the first optical path and the filtered modulated optical beam from the second optical path and to produce a filtered output signal comprising the at least one selected spectral component.

The device may use two whispering gallery mode (WGM) resonators as the two optical resonators which are tunable via an electro-optic effect. The tunable optical filter may include a third electro-optic whispering gallery mode resonator optically coupled to one of the two tunable optical resonators and tuned by the tuning control unit to effectuate a third order filter function in the tunable optical filter.

Alternatively, the tunable optical filter in the device may be implemented with a first optical waveguide optically coupled to the first and second optical resonators and to receive the modulated optical beam from the optical modulator, and a second, separate optical waveguide optically coupled to the first and second optical resonators to output the filtered modulated optical beam to the optical detector. The first and second optical resonators are directly optically coupled to each other in addition to optical coupling with each other via optical coupling to the first and second waveguides.

As another alternative, the tunable optical filter in the device may include a first optical waveguide optically coupled to the first and second optical resonators and to receive the modulated optical beam from the optical modulator and to output the filtered modulated optical beam to the optical detector, and a second, separate optical waveguide optically coupled to the first and second optical resonators. The first and second optical resonators are directly optically coupled to each other in addition to optical coupling with each other via optical coupling to the first and second waveguides.

Furthermore, the two optical resonators in the tunable optical filter of the device may be first and second optical resonators, respectively, and the tunable optical filter may further include third and fourth optical resonators. The first optical resonator receives the modulated optical beam from the optical modulator and the fourth optical resonator outputs the filtered modulated optical beam to the optical detector. The first, second, third and fourth optical resonators are optically coupled to one another in the following manner: the first optical resonator is optically coupled to the second and third optical resonators; the second optical resonator is further optically coupled to the fourth optical resonator; the third optical resonator is further optically coupled to the fourth optical resonator; and the second and third optical resonators are not directly coupled to each other and are indirectly coupled via the first and fourth optical resonators.

Other implementations described in this application perform the frequency tuning in the optical domain by tuning the frequency of the optical beam. For example, a method for filtering a signal includes applying a microwave or RF signal to an optical modulator to control optical modulation of an optical beam and to produce a modulated optical beam that carries the signal, optically filtering the modulated optical beam to reject undesired signal spectral bands in the modulated optical beam to produce a filtered optical beam that carries at least one selected signal spectral band, tuning a frequency of the optical beam to select the frequency of the at least one selected signal spectral band, combining a portion of the optical beam that is not modulated by the optical modulator and the filtered optical beam into a combined beam, and using an optical detector to convert the combined beam into a filtered microwave or RF signal that carries the at least one selected signal spectral band.

A device that implements the tuning of the frequency of the optical beam may include, for example, an input port to receive an input microwave or RF signal, a tunable laser to produce a continuous-wave laser beam and to tune a laser frequency of the laser beam, a first optical path to receive a first portion of the laser beam, a second optical path to receive a second portion of the laser beam, and a tuning control unit to tune the laser frequency of the tunable laser. The second optical path includes an optical modulator to modulate the second portion in response to the input signal to produce a modulated optical beam that carries the input signal, and an optical filter to filter the modulated optical beam to select at least one spectral component in the input signal while rejecting other spectral components and to output a filtered modulated optical beam that carries the at least one selected spectral component. Accordingly, the tuning control unit operates to tune the laser and thus change a frequency of the at least one selected spectral component. This device further includes an optical detector to combine the first portion from the first optical path and the filtered modulated optical beam from the second optical path and to produce a filtered output signal comprising the at least one selected spectral component.

In yet another implementation, a microwave or RF signal is applied to an optical modulator to control optical modulation of an optical beam and to produce a modulated optical beam that carries the signal. At least two cascaded optical resonators are used to optically filter the modulated optical beam to reject undesired signal spectral bands in the modulated optical beam to produce a filtered optical beam that carries at least one selected signal spectral band. A frequency of one of the two cascaded optical resonators is tuned to select the frequency of the at least one selected signal spectral band. A portion of the optical beam that is not modulated by the optical modulator and the filtered optical beam are combined into a combined beam. An optical detector is used to convert the combined beam into a filtered microwave or RF signal that carries the at least one selected signal spectral band.

Tunable filters and filtering techniques used for tunable RF receives use an input port to receive a non-optical input signal to be filtered, e.g., a microwave or RF signal, and an output port to export a filtered or processed non-optical signal, e.g., a filtered microwave or RF signal. The input signal is converted into optical domain via optical modulation of a continuous-wave optical beam and the modulated optical beam is then optically filtered to select desired microwave or RF spectral components. An optical filter with a high quality factor can produce ultra narrow linewidth to optically select one or more desired microwave or RF spectral components carried in the modulated optical beam. Such optical filtering of microwave or RF spectral components avoids use of microwave or RF filters that tend to suffer a number of limitations imposed by the electronic microwave or RF circuit elements. The filtered optical signal and a portion of the same continuous-wave optical beam are combined and sent into an optical detector. The output of the optical detector is used as the filtered or processed non-optical signal. Like the signal filtering, the frequency tuning of the filtering in these implementations is also achieved optically, e.g., by either tuning the frequency of the optical beam that is modulated by the optical modulator or an optical filter that is used to filter modulated optical beam.

Figure 4A:
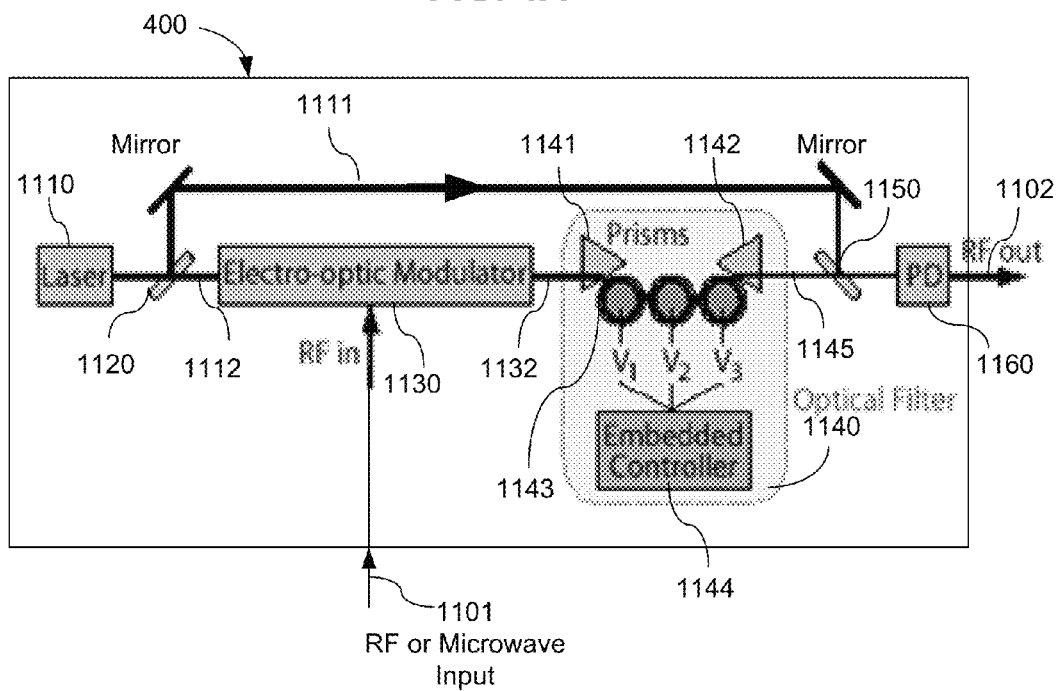
FIG. 4A shows one example of a tunable RF or microwave filter that uses a tunable optical filter for filtering and tuning the output RF or microwave signal.

FIG. 4A shows one example of a tunable microwave or RF filter 1100 based on optical filtering and tuning. The filter 1100 receives an input microwave or RF signal 1101 and produces a filtered output microwave or RF signal 1102 with one or more spectral components selected from the input spectral components in the input signal 1101. Inside the filter 1100, a laser 1100, e.g., a diode laser, is used to produce a continuous-wave laser beam. An optical beam splitter or coupler 1120 splits the laser beam into a first beam 111 along a first optical path and a second beam 1112 along a second, separate optical path. An optical beam combiner 1150 is used to combine the light beams from the two optical paths into a combined optical beam. An optical detector 1160 receives and converts the combined beam into the filtered microwave or RF signal 1102. The two optical paths formed by the beam splitter 1120 and the beam combiner 1150 create an interferometer: the upper first optical path serves as a reference while the filtering takes place in the lower second optical path. The upper first optical path may include an optical delay element to produce a delay that compensates for the group delay caused by the optical filter 1140 in the lower second optical path.

In this specific implementation, the optical filtering and tuning of the output signal 1102 are performed in the lower second optical path. The input RF or microwave signal 1101 is first up-converted into the optical domain using a broadband modulator. The signal filtering is done in optical domain using a tunable high-Q optical filter. The signal tuning is also done in the optical domain by tuning the optical filter to select one or more spectral components. In the lower second optical path, an optical modulator 1130, such as an electro-optic modulator, is used to modulate the second optical beam 1112 in response to the input signal 1101. This optical modulation produces a modulated optical beam 1132 that carries the microwave or RF spectral components in the input signal 1101. The operating bandwidth of the optical modulator 1130 is designed to be sufficiently broad to cover the signal frequencies of the input signal 101. The microwave or RF spectral components in the input signal 101 appear as optical sidebands at different optical frequencies from the laser frequency of the laser 1110. This process converts the microwave or RF spectral components into the optical domain. Therefore, signal filtering and frequency tuning can be performed optically.

Figure 4B:
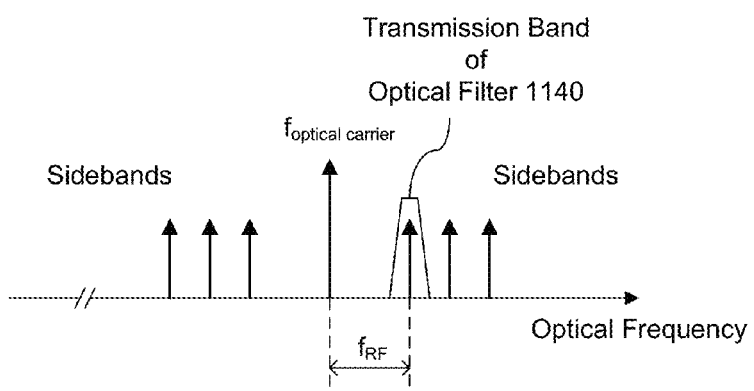
FIG. 4B is a chart illustrating an example of the spectrum of a modulated optical beam that carries the RF or microwave signals bands and the optical filtering by the tunable optical filter in FIG. 4A.

FIG. 4B illustrates the optical spectrum of the modulated optical beam 1132. The optical carrier is shown to be at the laser frequency ($f_{optical\ carrier}$) and the RF or microwave signal bands or spectral components originally in the input signal 101 are now carried by the optical carrier as optical sidebands. Each optical sideband is at an optical frequency and the frequency difference between the each sideband and the optical carrier is the microwave or RF frequency of the original signal band in the signal 1101.

Referring back to FIG. 4A, a tunable optical filter 1140 is placed in the second optical path between the optical modulator 1130 and the optical combiner 1150 to optically filter the modulated beam 1132 to produce a filtered optical beam 1145. A tuning control unit 1144 is provided to produce one or more control signals applied to the filter 1140 to tune the optical frequency of the filter's transmission band. If the quality factor of the optical filter 1140 is sufficiently high, the bandwidth of the optical filter 1140 can be sufficiently narrow to select only one sideband to transmit in the beam 1145 while rejecting two neighboring sidebands, all other sidebands and the optical carrier. The optical filter 1140 is designed to achieve this filtering operation. FIG. 4B shows that the optical filter 1140 is tuned to select the lowest sideband of the upper sidebands in the modulated optical beam 1132. As a result, the filtered optical beam 1145 has only one spectral component at the optical frequency of ($f_{optical\ carrier}+f_{RF}$).

The first optical beam 1111 in the first optical path is not modulated and thus has only the optical carrier. When the first beam 1111 and the filtered beam 1145 are combined at the optical detector 1160, the detection by the optical detector 1160 presents the beat signal between the optical carrier and the filtered sideband in the detector 1160. Therefore, the frequency of the output signal 1102 from the detector 1102 is the difference between the optical frequency of the filtered beam 145 and the first optical beam 1111, i.e., the filtered RF sideband at the frequency of $f_{RF}$. This converts the filtered signal down from the optical domain back to the RF and microwave domain. The optical filter 1140 can be tuned to select any of the signal sidebands carried by the modulated optical beam 132. As such, the frequency of the RF signal 1102 can be tuned.

The tunable optical filter 1140 may be implemented in various configurations. For example, the tuning may be achieved by thermal control of the resonator whose index, dimension, or both change with temperature, mechanical control of the resonator by changing the dimension of the resonator, electrical control, or optical control. Electro-optic materials may be used to control and tune the resonance frequency of the WGM resonator by an external control signal. For example, a single lithium niobate microresonator that supports whispering gallery modes is a tunable optical filter based on the electro-optic effect of the lithium niobate material and can be used as the filter 1140.

Figure 5A:
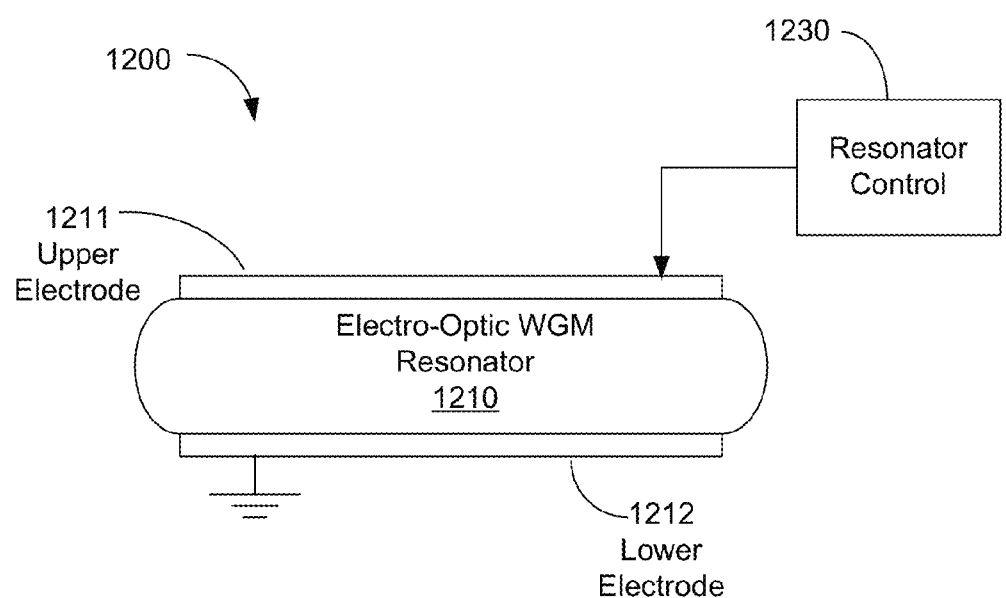
FIG. 5A shows a tunable electro-optic whispering gallery mode microresonator which may be used as a tunable optical filter.

FIG. 5A show an example of a tunable electro-optic WGM resonator 1200 having a WGM resonator 1210. The electro-optic material for the entire or part of the resonator 1210 may be any suitable material, including an electro-optic crystal such as Lithium Niobate and semiconductor multiple quantum well structures. One or more electrodes 1211 and 1212 may be formed on the resonator 1210 to apply a control electrical field in at least the region where the WG modes are present to control the index of the electro-optical material and to change the filter function of the resonator. Assuming the resonator 1210 has disk or ring geometry, the electrode 1211 may be formed on the top of the resonator 1210 and the electrode 1212 may be formed on the bottom of the resonator 1210. In implementation, the electrodes 1211 and 1212 may be in various geometries to apply a control voltage to tune the resonator. For example, the electrodes 211 and 1212 may be microstrip line electrodes. A tuning control unit 1230 such as a control circuit may be used to supply the electrical control signal to the electrodes 1211 and 1212. The control voltage may be a DC voltage to set the resonance peak of the resonator 1200 at a desired spectral location. The DC voltage may be adjusted by the control unit 1230 to tune the spectral position of the transmission peak when such tuning is needed. For dynamic tuning operations, the control unit 1230 adjusts the control voltage in response to a control signal to, e.g., maintain the transmission peak at a desired spectral position or frequency or to change the frequency of the transmission peak to a target position. In some other operations, the control unit 1230 may adjust the control voltage in a time varying manner, e.g., scanning the transmission peak at a fixed or varying speed or constantly changing the transmission peak in a predetermined manner.

Figure 5B:
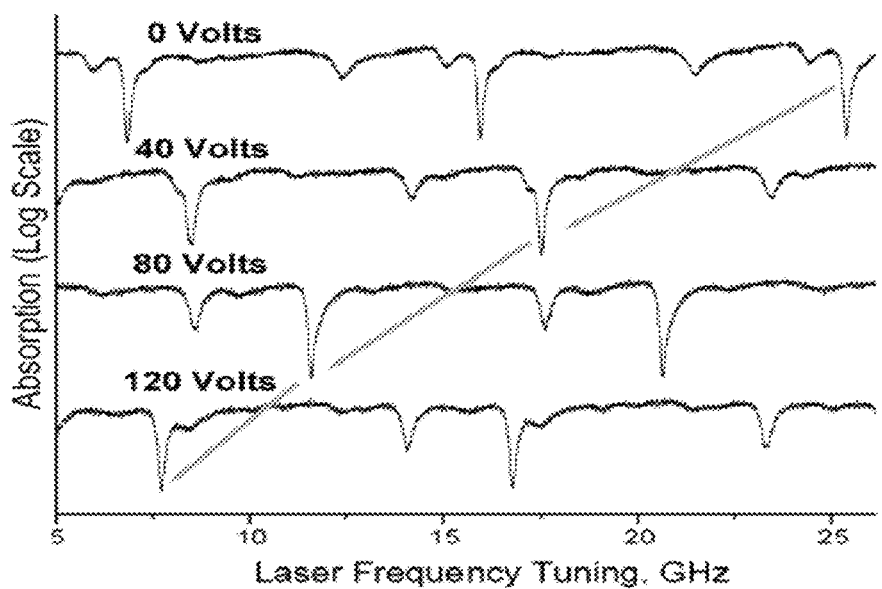
FIG. 5B shows measurements of optical absorption of a lithium niobate whispering gallery mode microresonator with a wide tuning spectral range of the whispering gallery modes under a tuning control voltage.

For example, a Z-cut $LiNbO_3$ disk cavity with a diameter of d=4.8 mm and a thickness of 170 μm may be used as the resonator 1210. The cavity perimeter edge may be prepared in the toroidal shape with a 100 μm radius of curvature. As an alternative to the strip electrodes shown in FIG. 5A, the top and bottom surfaces of the disk resonator may be coated with conductive layers for receiving the external electrical control signal. A metal such as indium may be used to form the conductive coatings. Tuning is achieved by applying and adjusting a voltage to the top and bottom conductive coatings. Each conductive coating may be absent on the central part of the resonator and are present at the perimeter edge of the resonator where WGMs are localized. FIG. 5B shows optical absorption measurements on a lithium niobate microresonator showing a wide tunability of the whispering gallery modes with application of a voltage. The curves are offset vertically for clarity.

Such a single-resonator filter has a Lorentzian lineshape in its spectral transmission and presents a less than ideal passband with a relatively slow roll-off from the center transmission peak. When the signal spectral bands in the input signal 1101 are close to one another, the single-resonator filter may not be sufficient to separate neighboring bands. In various implementations, two or more such tunable microresonators may be optically cascaded together in series to create a multipole optical filter with a flatter passband and sharper spectral roll-offs. Light can be evanescently coupled between the closely-spaced (e.g., about 1 μm) or directly contacted microresonators.

The shape of the passband function for such a cascaded multi-resonator filter may be controlled by adjusting a number of device parameters. For example, the number of microresonators sets the order of the filter and directly determines how sharply the filter response rolls-off outside the passband. The quality factors of microresonators can determine the natural linewidth of the filter function. Tunable lithium niobate microresonators may be fabricated to produce varying bandwidths, such as narrow linewidths of about 10 MHz or less, or broad linewidths at tens of MHz. The physical gaps that separate the cascaded microresonators (and the coupling prisms at either end of the series from the first and last microresonators) can be adjusted to control the coupling strengths. The gaps may be fixed in certain implementations and adjustable for maximum flexibility in dynamically reconfiguring the filter function in other implementations. Different control voltages to different microresonators may be used to provide desired offsets of the different filter poles relative to a selected center of the filter passband to achieve a desired filter spectral profile. The tuning control unit 144 may include an embedded logic unit that dynamically adjusts the offsets of the filter poles. Accurate placements of the poles can minimize ripple in the final filter passband.

The design of multi-pole optical filters with microresonators may be analogous to design multi-pole RF filters to a certain extent but the design parameters are very different. For example, the equivalent RF Q factors of microresonators are much higher than many RF filters. The equivalent RF Q factor a Microresonator is the optical Q factor multiplied by a ration of the RF frequency over the optical frequency. Hence, at the optical wavelength of 1550 nm, the ratio is about $5 \times 10^{-5}$ and an optical Q factor of $10^9$ is equivalent to an RF Q factor of about $5 \times 10^4$.

Figure 6A:
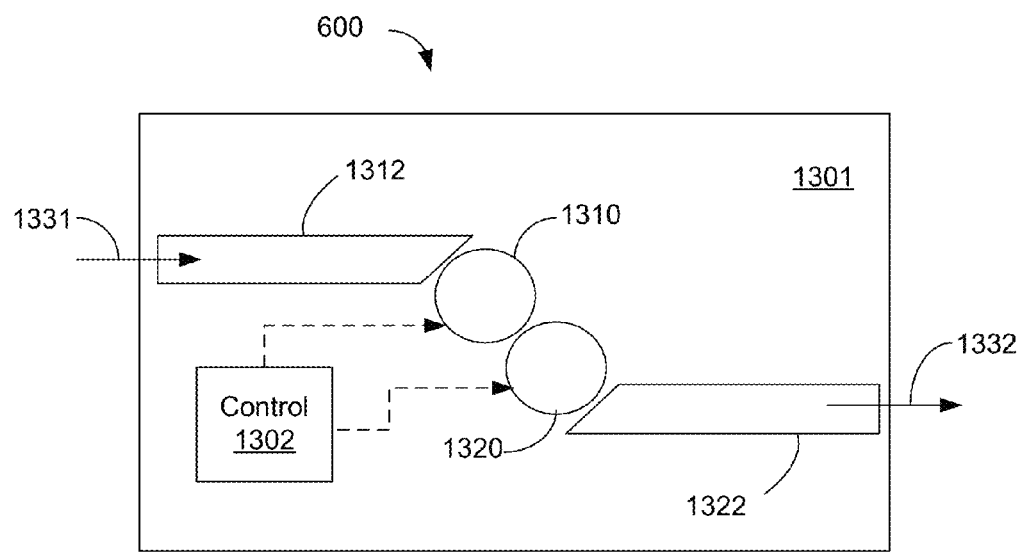
FIG. 6A shows a two-pole tunable optical filter that includes two coupled whispering gallery mode microresonators.

FIG. 6A shows an exemplary tunable two-resonator filter 600 having two cascaded WGM resonators 1310 and 1320. In some implementations, both resonators may have approximately the same diameter or dimension to have similar quality factors. In certain other implementations, it may be advantageous to use different resonators 1310 and 1320 with different geometries or physical dimension to use their difference in the spectral profile to produce the desired composite filter function. The resonators 1310 and 1320 are placed close to or in contact with each other to allow for direct optical coupling under proper resonance conditions. Alternatively, an optical coupling mechanism may be placed between the resonators 1310 and 1320 to assist and facilitate the inter-resonator optical coupling. An input optical coupler 1312 is placed near or in contact with the first resonator 1310 to couple an input optical signal 1331 into the first resonator 1310 of the filter 600. An output optical coupler 1322 is placed near or in contact with the second resonator 1320 to couple optical energy inside the second resonator 1320 out to produce an output optical signal 1332 as the transmission of the filter 600. As illustrated, a support base 1301, such as a substrate, may be used to hold and fix the components of the filter 600 in position. A control unit 1302 is provided to control and tune at least one of the resonators 1310 and 1320 to make the filter 600 tunable. In some implementations, both resonators 1310 and 1320 may be tunable.

Figure 6B:
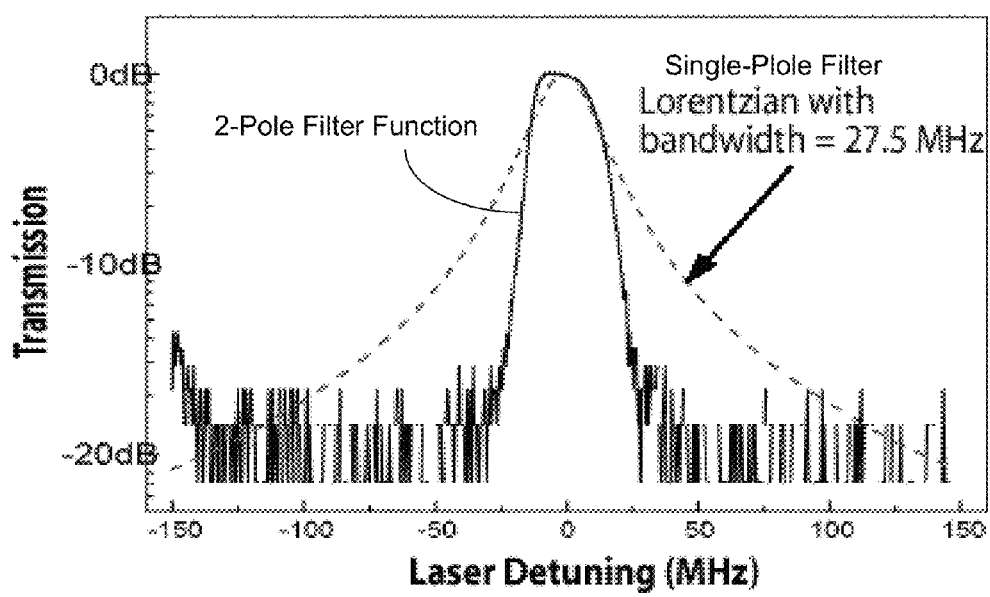
FIG. 6B shows a measured transmission spectrum of a 2-pole optical filter with two silica whispering gallery mode microresonators to illustrate a sharper roll-off than a Lorentzian transmission spectrum of a single microresonator. The floor at −20 dB is an artifact of the measurement and does not represent a limitation of the filter.

FIG. 6B shows a measured spectrum of a 2-pole filter with two silica microresonators coupled in series. A single pole filter function of a single microresonator is shown in a dashed curve as a comparison. The measured 2-pole filter function has a flatter top and sharper spectral roll-off and hence is better suited for filtering different signal bands as illustrated in FIG. 4B.

Figure 7:
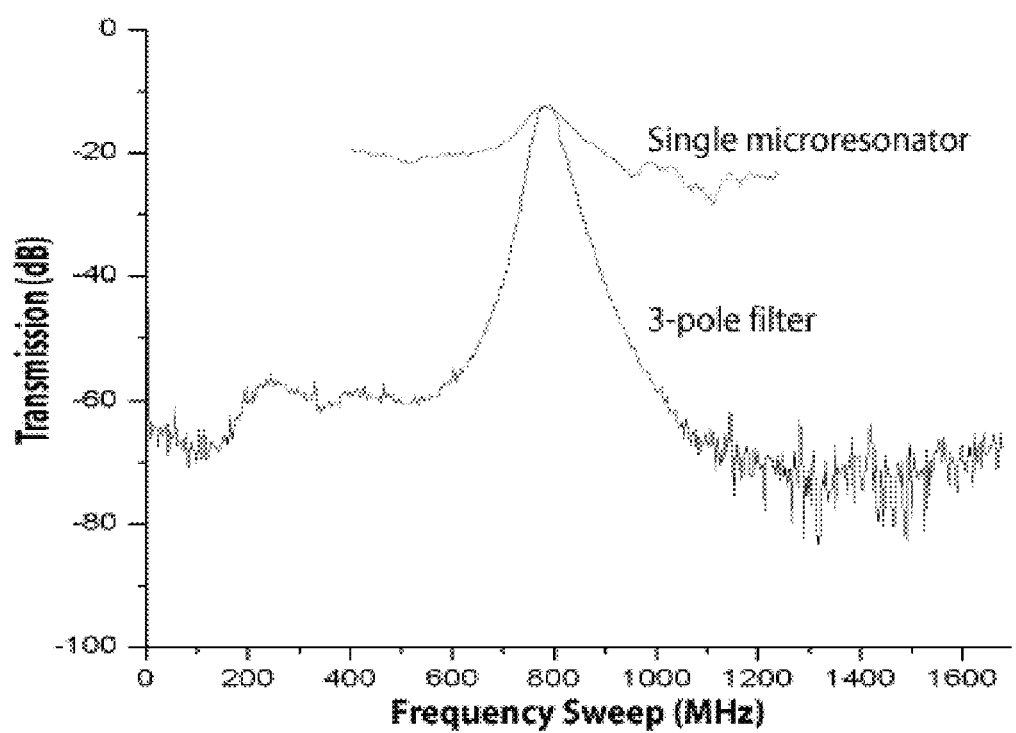
FIG. 7 shows a measured transmission spectrum of a 3-pole lithium niobate optical filter with three cascaded lithium niobate whispering gallery mode microresonators as shown in FIG. 1A. The overlay shows the response of a single-resonator filter with its peak normalized to the peak of the 3-pole response.

FIG. 7 shows measured filter functions for a 3-pole microresonator filter constructed from three lithium niobate microresonators and a single microresonator filter. Tunability was exploited only over a narrow range to set the frequency offsets of the filter poles precisely and optimize the filter transmission function. The filter allows for wide (tens of gigahertz) tunability of filter center frequency with preservation of the shape of the filter's multi-pole transmission function (and thus the filter's performance characteristics) over the same broad range. Additionally, the bandwidth of the filter can be varied by adjusting the loading of resonators by means of changing one or several of the coupling gaps in the filter.

A number of technical issues associated with implementation of multi-resonator filters are addressed below. The electro-optic effect in lithium niobate is evident in FIG. 5B. Hence, the transmission peak frequencies and the corresponding control voltages response should be measured throughout the operating range carefully so that the filter control can be programmed to tune the filter to any desired frequency. The voltages applied to different microresonators in a filter can be controlled independently to ensure proper spacing of the offsets of the pole frequencies. As a filter tunes over its full operating spectral range, the whispering gallery mode amplitudes, shapes and coupling constants of the microresonators may vary slightly. Such variations can be measured and calibrated to control the filter function during tuning. Deliberately shifting the offsets of the pole frequencies relative to the tunable center of the bandpass may be used to compensate for these variations and preserve the optimal shape of the filter function. This additional level of control should also permit some dynamic adjustment of the filter's bandwidth.

Referring back to FIG. 4A, a tunable 3-pole filter is shown as an example for the tunable filter 1140. Three electro-optic WGM microresonators 1143 are cascaded in series between an input optical coupler 1141 and an output optical coupler 1142. The couplers 1141 and 1142 are shown as prisms but other implementations such as angled fiber tip couplers and photonic gap material couplers may also be used. Three separate control voltages V1, V2, and V3 are generated from the control unit 1144 to control and tune the three resonators 1143, respectively. In other implementations, four or more microresonators may be cascaded to form desired final filter functions.

The tunable optical filter 1140 in FIG. 4A may also be implemented by tunable filters that include two or more optical resonators and two separate optical waveguides. The two or more optical resonators that are optically coupled with one another to produce an optical resonance transmission peak that is narrower than the natural transmission linewidth of each resonator. The optical coupling of the resonators causes optical interference between the resonators (e.g., interference of their optical delays) that leads to the narrow transmission peak. The resonators may be directly coupled with one another, indirectly coupled with one another via optical waveguides, or coupled both directly between two adjacent resonators and indirectly via waveguides. At least one of the resonators is tunable to change its resonance frequency to adjust the center frequency of the narrow transmission peak and the optical delay in light spectrally located in the narrow transmission peak. Notably, the described device designs and techniques are applicable to other electromagnetic frequencies outside the optical spectral range, such as the microwave and millimeter frequencies where microwave resonators and waveguides, for example, are used to implement the desired wave coupling and tuning in frequency.

The specific examples described here are in optical domain and use optical waveguides and whispering gallery mode resonators. In particular, device designs with a parallel configuration of two interacting whispering-gallery-mode optical resonators are described to show a narrowband modal structure as a basis for a widely tunable delay line. The optical coupling can be optimized so that such devices produce an unusually narrow spectral feature with a much narrower bandwidth than the loaded bandwidth of each individual resonator.

This effect of the devices described here is analogous to the phenomenon of electromagnetically induced transparency (EIT) in resonantly absorbing quantum systems. The quantum-mechanical interference of spontaneous emissions from two close energy states coupled to a common ground state results in ultranarrow resonances in EIT. The devices and techniques described here produce similar narrow resonances based on classic cavity modes and the interference between direct and resonance-assisted indirect pathways for decays in two coupled resonators. This is the same Fano resonance for optical resonators that has been shown to result in sharp asymmetric line shapes in a narrow frequency range in periodic structures and waveguide-cavity systems.

The above specific examples of tunable RF or microwave filters based on optical filtering and tuning use optical tunability of the optical filter 1140 in FIG. 4A to optically select a spectral component or signal band from the original input signal 1101 and thus tune the frequency of the output signal 1102. The optical tuning is essentially to change the frequency difference between the optical carrier of the modulated optical beam 1132 and the center frequency of the transmission passband of the optical filter 1140 so that the optical filter can optically select any of the signal bands in the input signal 1101 carried by the optical carrier as the output signal 1102.

Hence, the optical tuning may be achieved by tuning either one or both of the optical carrier frequency of the optical beam and the center frequency of the transmission passband of the optical filter. In some implementations, it is beneficial to use a tunable filter as shown in FIG. 4A and a fixed laser. In other implementations, it may be beneficial to tune the laser frequency while using a fixed optical filter. Hence, optical tuning may be achieved by tuning the frequency of the optical carrier, e.g., the laser frequency of the laser 1110 relative to the center frequency of the transmission passband of the filter 1140. Accordingly, the filter 1140 is replaced by a fixed narrowband high-Q optical filter and the laser 1110 is replaced by a tunable laser that can be tuned over the tuning range of the tunable RF or microwave filter. It is further contemplated that the laser and the optical filter may both be tuned to expand the tuning range of the tunable RF or microwave filter.

Specific tunable RF and microwave filters with tunable lasers and fixed optical filters are described below as examples.

Figure 8A:
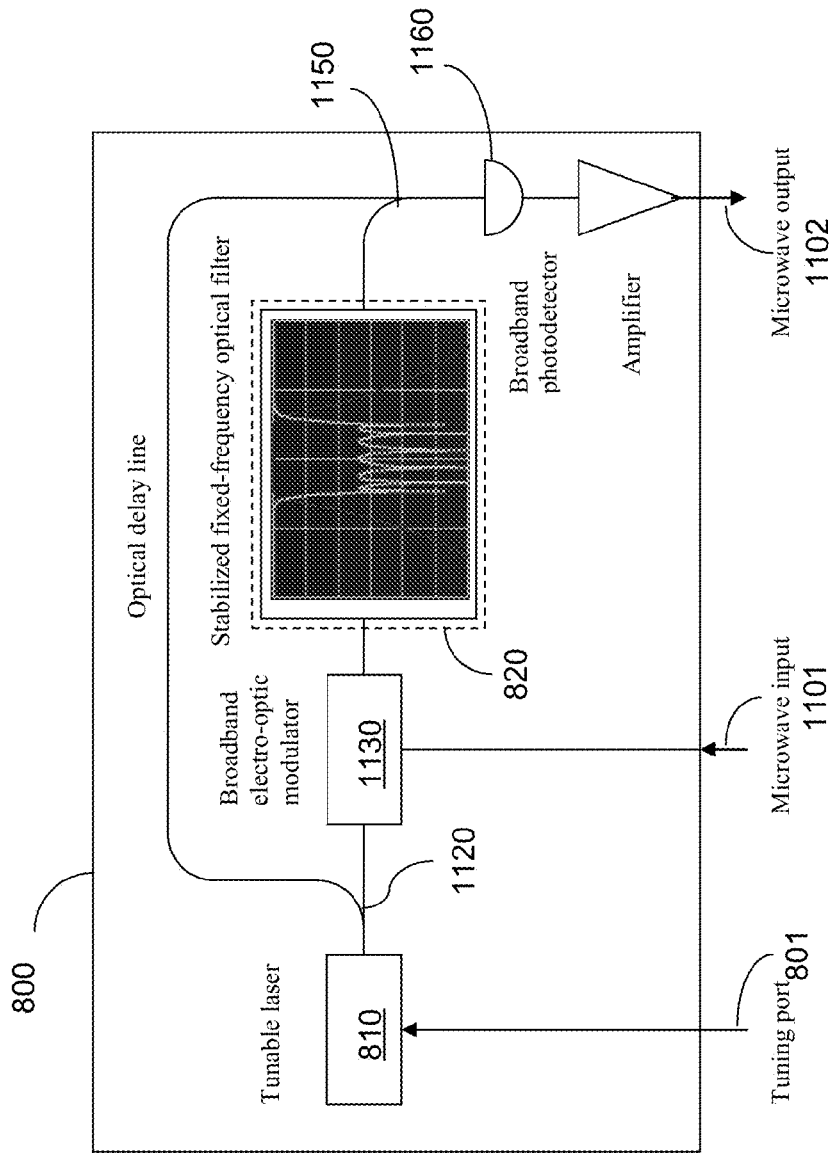
FIGS. 8A-8B show an example of a tunable RF or microwave filter with a tunable laser to tune the laser frequency relative to the center frequency of the transmission band of the optical filter in tuning the frequency of the filtered RF or microwave output signal.

FIG. 8A shows an example of a tunable RF or microwave filter 800 that uses a tunable laser 810 to achieve the tuning and a fixed optical filter 820 to achieve the filtering. The RF or microwave signal 1101 is up-converted into the optical domain using the broadband modulator 1130 and the filtering is done in optical domain using the fixed frequency high-Q optical filter 920 which may be a single-pole or a multi-pole filter. The RF signal is restored by recombining the filtered optical beam with optical carrier on the broadband photodetector 1160. The laser frequency of the laser 810 is controlled by and tuned in response to a tuning control signal 801 received at a tuning port from a control unit.

Figure 8B:
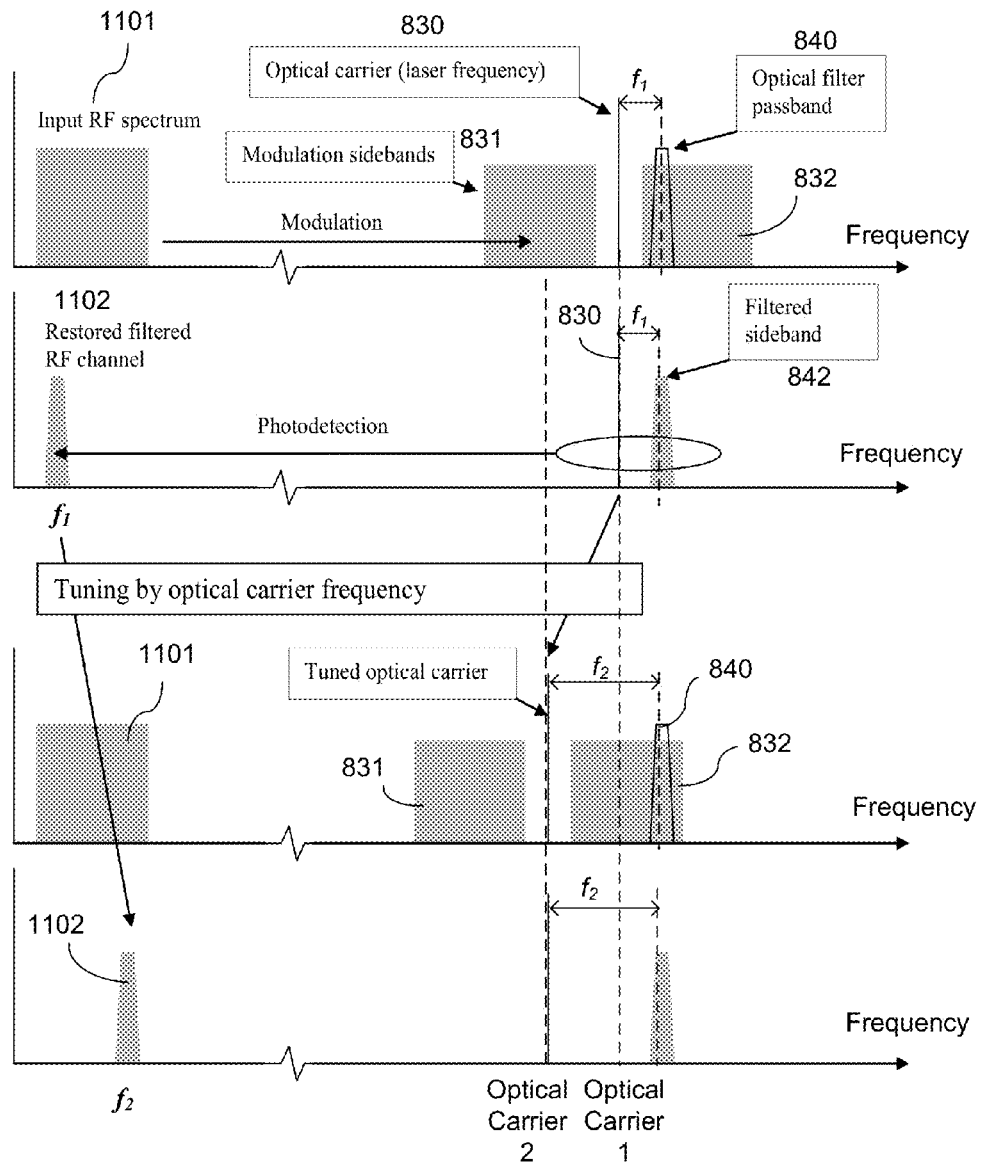

FIG. 8B illustrates operation of the filter 800 in FIG. 8A. The input RF signal 1101 has an input RF spectrum as shown and is converted via the optical modulation by the modulator 1130 into two modulation sidebands 831 and 832 on opposite sides of the optical carrier 830. Any one of modulation sidebands 831 and 832 may be used to select a particular RF signal band as the output signal 1102. As an example, the laser 810 is tuned to place a signal band in the modulated optical beam at $(f_{optical\ carrier}+f1)$ within the fixed passband 840 of the optical filter 820. The filtered signal band out of the optical filter 820 is represented by numeral 842. The optical detection of the optical carrier 830 and the filtered signal band 842 produces the output signal 1102 at the selected frequency f1.

If the laser 810 is subsequently tuned to change the optical carrier 830 to a different optical carrier, e.g., the optical carrier 2 at a lower frequency than the initial optical carrier 1, this tuning shifts frequencies of the modulation sidebands 831 and 832 to lower frequencies by the same amount. This change in the optical carrier frequency places a different part of the upper modulation sideband 832 within the fixed passband 840 of the optical filter 820 to select a signal band with a higher frequency f2 as the filtered output signal 1102 from the optical detector 1160.

Figure 9:
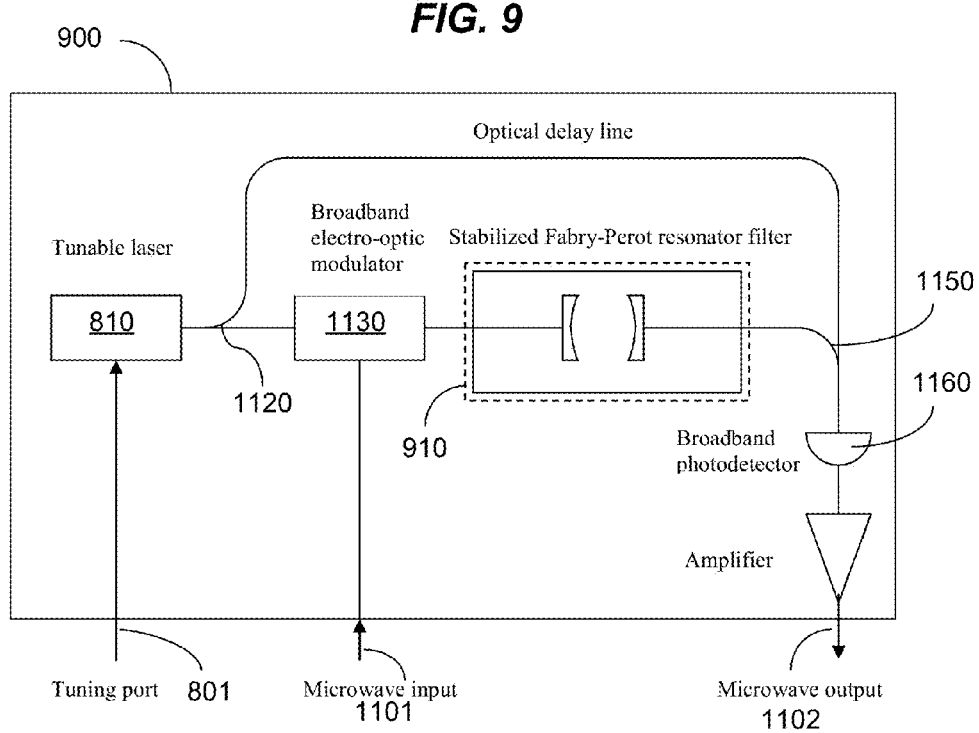
FIGS. 9 and 10 show two exemplary implementations based on a tuning via tuning a tunable laser.
Figure 10:
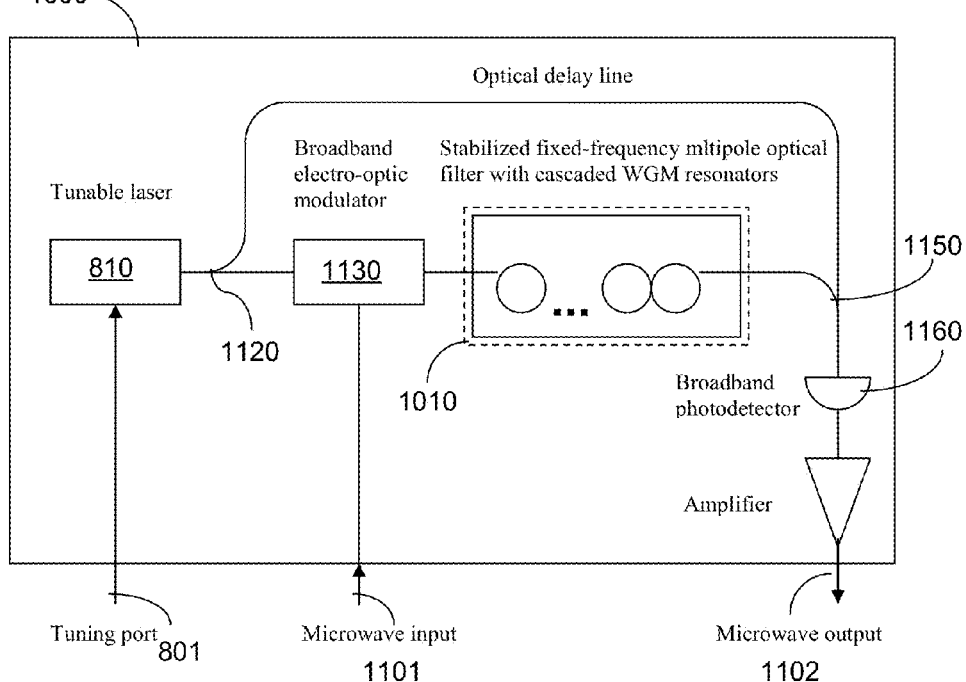

FIGS. 9 and 10 show two examples of tunable RF or microwave filters based on the above tuning of the tunable laser. In the filter 900 in FIG. 9, a Fabry-Perot resonator filter 910 is used as the filter 820 in FIG. 8A. The filter 1010 in FIG. 10 uses a multi-pole filter with cascaded WGM microresonators as the filter 820 in FIG. 8A. The multi-pole filter 1010 may be formed by cascaded ring resonators, microsphere resonators, or toroidal resonators that support whispering-gallery modes.

This use of the tunable laser 810 for tuning the frequency of the filtered RF or microwave signal 1102 can simplify the construction of the optical filter 820 because a fixed filter can be used as the filter 820 without the frequency tuning mechanism. Tunable multi-pole optical filters can be complex because changes in the multi-pole variants are to be synchronized during the tuning in order to maintain the desired multi-pole filter function. One or more resonators used in the fixed filter 820 may still be tunable filters to allow for tuning of individual resonators by the electro-optic or other effects to set the desired offsets of resonance frequencies so that a desired initial spectral profile of the filter passband can be achieved. Alternatively, UV-sensitive materials may also be used to form the resonators for the filter 820 so that UV trimming can be used to modify the refractive indices of the resonators and thus control the resonance frequencies of the resonators by exposing the resonators to UV light. After the initial filter profile is set, the optical filter 820 may be stabilized. The RF filter tuning is then achieved by tuning the laser frequency.

Agile frequency tuning in lasers, such as diode lasers and diode-based lasers, is well developed and can be implemented by different methods. For example, the driving current in distributed feedback (DFB) semiconductor lasers can be changed to tune the laser frequencies. Typical range of frequency tuning in some DFB lasers in the communication band 1550 nm is about 60-80 GHz, with an optical laser linewidth of about 1 MHz. Such tunable lasers are suitable for use in tunable RF or microwave filters with a tunable transmission passband of about 20 MHz and more.

Additional examples of tunable receives in the RF, microwave and millimeter ranges are provided below.

In one aspect, a device is described to include a first laser to produce a first continuous-wave (CW) laser beam at a first laser frequency; an optical modulator to receive the first CW laser beam and an input RF signal and operable to modulate the first CW laser beam in response to the input RF signal to produce a modulated optical beam that carries the input RF signal; a tunable optical filter to filter the modulated optical beam from the optical modulator to select at least one spectral component in the modulated optical signal while rejecting other spectral components and to output a filtered modulated optical beam that carries the at least one selected spectral component; a filter control unit to tune a center frequency of the tunable optical filter to tune the at least one selected spectral component; a second laser to produce a second CW laser beam at a second laser frequency; an optical detector to receive both the filtered modulated optical beam from the tunable optical filter and the second CW laser beam to produce a receiver output signal at an output frequency; and a control unit to lock the first and second lasers in phase relative to each other and to control the first and the second lasers to tune a difference between the first and the second laser frequencies in response to the tuning of the center frequency of the tunable optical filter to maintain the output frequency of the receiver output signal at a desired fixed frequency.

In another aspect, a device is described to include an electrical port to receive an input electrical oscillation signal at an input carrier frequency in a radio frequency, microwave, or millimeter wave spectral range; a first laser to produce a first continuous-wave (CW) laser beam at a first laser frequency; an optical modulator to receive the first CW laser beam and the input signal and operable to modulate the first CW laser beam in response to the input signal to produce a modulated optical beam that carries the input signal; a tunable optical filter to filter the modulated optical beam from the optical modulator to select at least one spectral component in the modulated optical signal while rejecting other spectral components and to output a filtered modulated optical beam that carries the at least one selected spectral component; a second laser to produce a second CW laser beam at a second laser frequency; and an optical detector to receive both the filtered modulated optical beam from the tunable optical filter and the second CW laser beam to produce a receiver output signal at an output frequency. In this device, the first and second lasers are phase locked relative to each other. A phase locking unit can be provided in this device to lock the first and second lasers in phase and to control a difference between the first laser frequency and the second laser frequency to tune the output frequency of the receiver output signal. The center frequency of the tunable optical filter can be tuned to the input carrier frequency and this use of the tunable optical filter can be used to achieve a wide tuning range for the device to cover, e.g., one or more spectral ranges in the radio frequency, microwave, and millimeter wave spectra.

In yet another aspect, a method is described to include using an input electrical oscillation signal at an input carrier frequency in a radio frequency, microwave, or millimeter wave spectral range to control optical modulation of a first continuous-wave (CW) laser beam at a first laser frequency from a first laser to produce a modulated optical beam that carries the input electrical oscillation signal; optically filtering the modulated optical beam to select at least one spectral component in the modulated optical signal while rejecting other spectral components to output a filtered modulated optical beam that carries the at least one selected spectral component; mixing the filtered modulated optical beam with a second CW laser beam at a second laser frequency from a second laser which is phase locked relative to the first laser to produce a mixed optical signal; and using an optical detector to convert the mixed optical signal into a receiver output signal at an output frequency.

Figure 11:
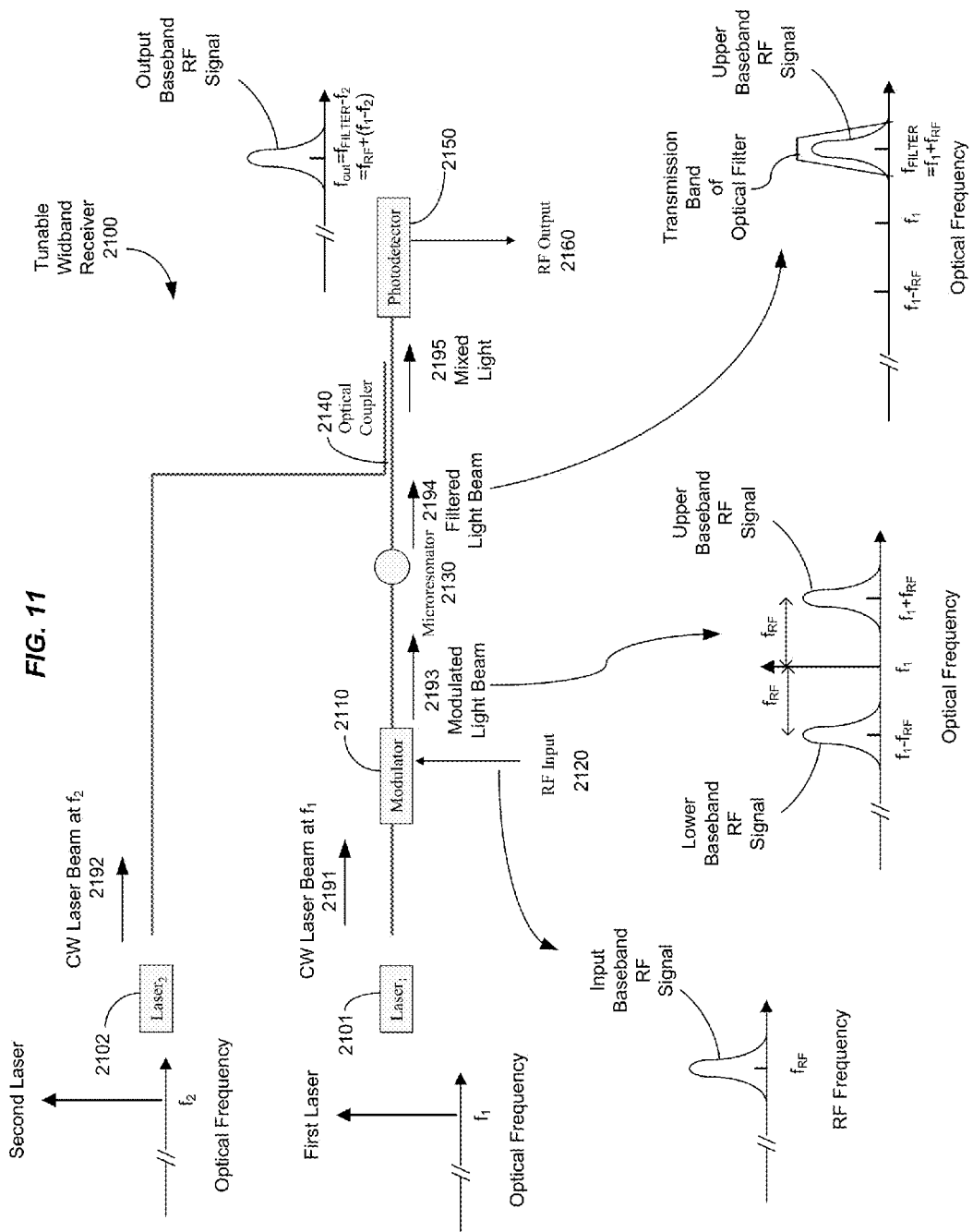
FIG. 11 shows the design and operation of an exemplary tunable wideband receiver for receiving an RF, microwave or millimeter signal based on photonics technology, where two phase-locked lasers are used.

FIG. 11 shows an example of a tunable wideband receiver 100 which includes a first laser 2101, a second laser 2102, an optical modulator 2110, a tunable optical filter 2130, an optical coupler 2140 and an optical detector 2150. An electrical port is provided to receive an input electrical oscillation signal 2120 at an input carrier frequency in a radio frequency (RF), microwave, or millimeter wave spectral range. Examples described in this application assume the input signal 2120 is an RF signal at an RF carrier frequency $f_{RF}$. The output of the optical detector 2150 is the receiver output signal 2160. Electronic components, such as amplifiers and filters, may be included in the signal path of the signal 2120 or 2160. The optical modulator 2110 provides the interface between the input electrical signal and the optical part of the receiver 2100 and the optical detector 2150 provides an interface between the optical part of the receiver 2100 and the receiver output signal 2160.

The first laser 2101, e.g., a diode laser or a solid-state laser, is used to produce a first continuous-wave (CW) laser beam 2191 at a first laser frequency f1. The second laser 2102, e.g., a diode laser or a solid-state laser, is used to produce a second CW laser beam 2192 at a second laser frequency f2. These two laser frequencies f1 and f2 are generally different in most operations and can be close to each other or the same in some operations. At least one of the two lasers 2101 and 2102 is tunable to allow for a phase locking mechanism to be implemented to lock the lasers 2101 and 2102 to have a fixed phase relative to each other. The frequency different between the two lasers 2101 and 2102 can be tuned by tuning the one tunable laser or both tunable lasers to set the carrier frequency of the receiver output signal 2160. This use of two phase locked lasers 2101 and 2102 can achieve up conversion and down conversion of the input carrier frequency $f_{RF}$.

The optical modulator 2110 is used to receive the first CW laser beam 2191 and the input signal 2120 as a modulation control signal. The modulator 2110 modulates the first CW laser beam 2191 in response to the input signal 2120 to produce a modulated optical beam 2193 that carries the input signal 2120. The modulator 2110 can be a phase modulator or an amplitude modulator. An electro-optic phase or amplitude optical modulator, for example, can be used as the modulator 2110. Another example of the modulator 2110 is a semiconductor optical modulator formed from a multiple quantum well structure that responds to an electrical control signal to perform optical modulation.

Spectra of the input signal 120 and the optical signals 2191, 2192 and 2193 are illustrated by the inserts in FIG. 11. The input signal 2120 can be modulated to carry a baseband signal that contains data and is generated by modulating the baseband signal at a predetermined bit rate onto an RF carrier signal at the RF carrier frequency $f_{RF}$. As one example, the modulated optical signal 2193 can include upper and lower modulation sidebands at (f1+$f_{RF}$) and (f1−$f_{RF}$), respectively, and the original optical carrier at f1. The sidebands carry the baseband signal in the input signal 2120.

The tunable optical filter 2130 is placed downstream from the modulator 2110 in the optical path of the modulated beam 2193. The filter 2130 is a bandpass filter with a tunable center frequency $f_{FILTER}$ to selectively transmit one selected spectral segment in the input signal 2120, who is carried by the modulated optical beam 2193, and to reject all other components. For example, the center frequency $f_{FILTER}$ of the transmission band of the optical filter 2130 can be tuned to any desired part of the input signal, e.g., one of the sidebands in the input signal 2120, as the selected spectral segment so that the spectral components within the bandwidth of the optical filter 2130 can be selected for output in the output signal 2160. The bandwidth of the optical filter 130 is designed to be sufficiently broad to cover a desired spectral segment in the input signal 2120 as the receiver output 2160 and is sufficiently narrow to reject the optical carrier and the other sidebands. Therefore, if the baseband signal of the input signal 2120 shown in FIG. 11 is to be selected for the receiver output signal 2160, the bandwidth of the filter 2130 can be set to be equal to or greater than the bandwidth of the baseband signal in the input signal 2120. Therefore, the combination of the optical modulator 2110 and the tunable optical filter 2130 allows the optical filter 2130 to select a spectral segment carried by the input electrical signal 2120 in the RF, microwave, or millimeter spectral range in the optical domain. The selected spectral segment can be a portion of a baseband signal carried by an RF, microwave or millimeter carrier in the input signal 2120, or an entire baseband signal and its RF, microwave or millimeter carrier of out multiple RF, microwave or millimeter carriers in the input signal 2120. The filter 2130, therefore, outputs a filtered modulated optical beam 2194 that carries the selected spectral component. The tunable optical filter 2130 can be in various configurations, such as a microresonator that supports one or more whispering gallery modes, a micro ring resonator, or a Fabry-Perot resonator. Notably, such an optical resonator can be tuned over a wide range in the RF, microwave, and millimeter wave ranges that is difficult to achieve by using electronic filters or electronic filter banks. This tunable optical filter 2130 can be tuned over the spectral range of various optical sidebands carried by the modulated signal 2193 to select a desired sideband or a portion of a sideband.

Downstream from the optical filter 2130 is the optical coupler 2140 that is also optically coupled to receive the second CW laser beam 2192 from the second laser 2102. The optical coupler 2140 is designed to combine the beams 2192 and 2194 together to produce a combined beam 2195. The optical detector 2150 is used to receive the combined beam 2195 and converts the received light into the receiver output signal 2160 at an output signal frequency $f_{out}$. The optical detector 2150 is a fast photodetector which detects the beat between the two beams 2192 and 2194. As a result, the frequency of the receiver output signal 2160 is $f_{out}=f_{FILTER}-f2$ when $f_{FILTER}>f2$ or $f_{out}=f2-f_{FILTER}$ when $f_{FILTER}<f2$. In the example in FIG. 11, $f_{FILTER}=f_{FR}+f1$ and $f_{out}=f_{RF}+(f1-f2)$.

Notably, the frequencies of the two lasers 2101 and 2102 can be controlled so that the difference (f1−f2) can be zero, a positive number or a negative number to. When the two lasers 2101 and 2102 are operated at the same laser frequency (f1=f2), the receiver output signal 2160 a filtered version of the input baseband signal. When the two lasers 2101 and 2102 are operated at the different laser frequencies (f1≠f2), the receiver output signal 2160 is a up-converted or down-converted baseband signal with the spectral component selected by the optical filter 2130. As such, the difference (f1−f2) can be controlled to place the output frequency $f_{out}$ at any desirable frequency desired in a particular application for the receiver 2100. In the example shown in FIG. 11 when the filter 2130 is at $f_{FILTER}=f_{FR}+f1$, if the laser frequency f2 of the second laser is set to be higher than the first laser 2101, a down conversion can be achieved from DC where $f_{out}=0$ (when the frequency of the laser 2102 is higher than the laser 2101 by $f_{RF}$) to $f_{out}=f_{RF}$ (when two lasers are at the same frequency). Therefore, the use of the two lasers 2101 and 2102 provides a flexible and easy implementation of frequency up conversion and down conversion.

In some applications, the receiver 2100 can be operated to scan the optical filter 2130 through the different spectral components within the baseband signal carried by an RF, microwave or millimeter carrier in the input signal 2120 while maintaining the output frequency $f_{out}$ of the receiver output signal 2160 at a fixed IF frequency to allow for a processing circuit operated at the fixed IF frequency $f_{out}$ to process the output signal 2160 to extract information in the different spectral components in the input signal 2120. Referring to FIG. 11, when the first laser 2101 is operated at a fixed laser frequency f1, as the optical filter 2130 is tuned to change its center frequency $f_{FILTER}$ relative to the laser frequency f1 to scan through different spectral components of the input signal 2120 in the optical domain, the frequency f2 of the second laser 2102 must be tuned to track and synchronize with the tuning of the filter center frequency $f_{FILTER}$ to maintain $f_{out}=f_{FILTER}-f2$ or $f_{out}=f2-f_{FILTER}$ at the fixed IF frequency. For example, if the IF frequency $f_{out}$ is set to be 500 MHz, then the laser lock will be at an offset corresponding to the center frequency $f_{FILTER}$ of the filter 130 plus 500 MHz. The laser 2102 can be locked to be 500 MHz away from the center frequency $f_{FILTER}$ of the filter 2130 and maintains this spacing as the filter 2130 tunes. This configuration allows generation of the IF signal at the output of the photodetector 2150 utilizing the photonic filter 2130 and this second LO laser 2102.

The above optical processing in the receiver 2100 in processing an RF, microwave, or millimeter wave signal avoids use of electronic filters and components that tend to suffer significant signal loss, a limited tuning range and other limitations inherent in the electronic microwave or RF circuit elements. In the receiver 2100, both tuning and filtering of an RF, microwave, or millimeter signal are performed optically using optical components in the optical domain.

Figure 12:
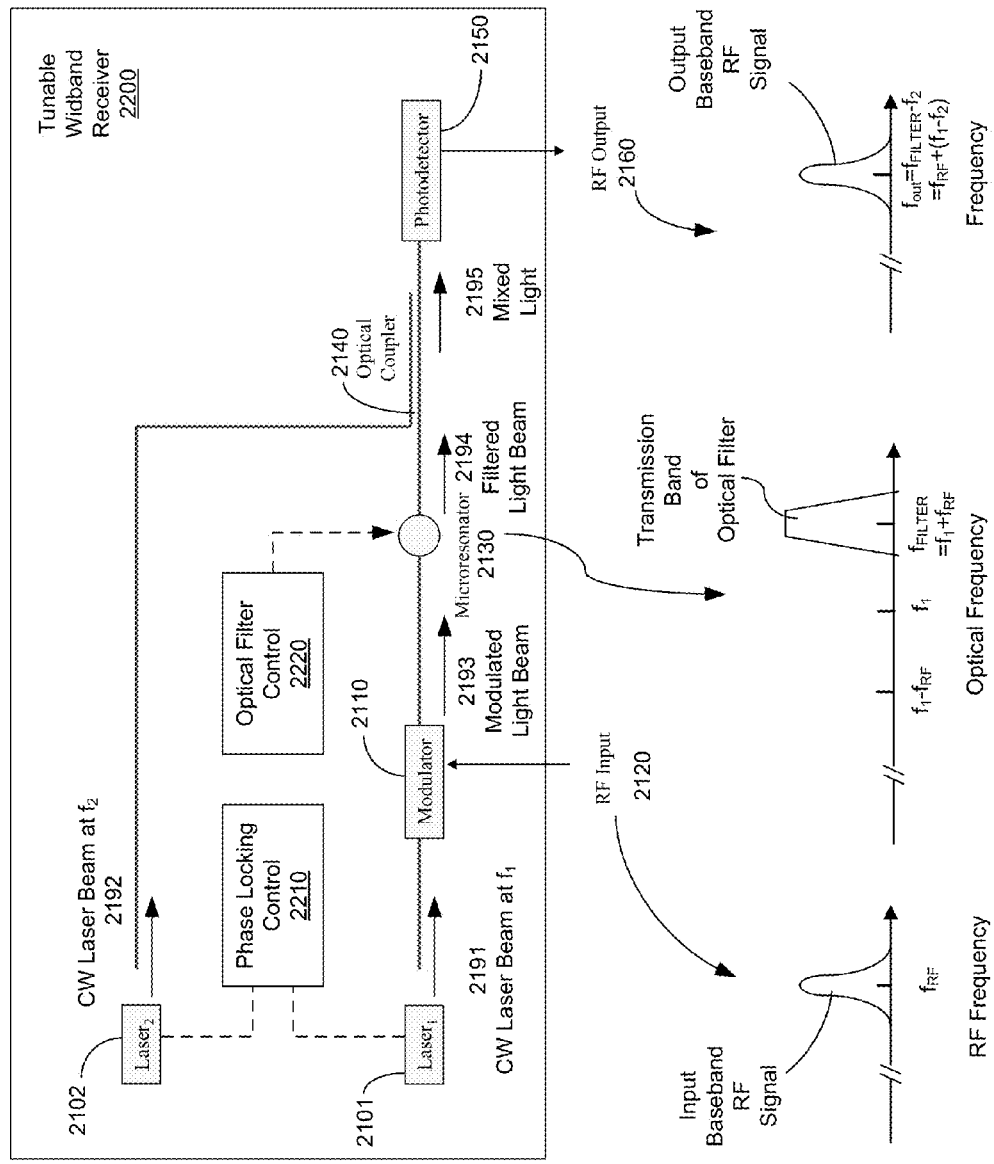
FIG. 12 shows laser tuner, phase locking control and optical filter control in the receiver in FIG. 11.

FIG. 12 shows a tunable wideband receiver 2200 can include a phase locking control module 2210 to lock the relative phase between the two lasers 2101 and 2102 so that the difference in their laser frequencies f1 and f2 is controlled at a fixed value and can be tuned to a different value if needed. At least one laser is a tunable laser to allow for this phase locking control. Hence, one implementation can use one fixed laser (e.g., the laser 2101) and one tunable laser (e.g., the laser 2102) and another implementation can use two tunable lasers as the lasers 2101 and 2102. The phase locking control module 2210 may be configured to detect a drift in frequency between the two lasers 2101 and 2102 and tune the tunable laser to negate the drift so that a desired frequency difference (f1−f2) between the two lasers 2101 and 2102 is maintained. As mentioned above, as the optical filter 2130 is tuned relative to the laser frequency f1 from one spectral component to another spectral component in the input signal 2120, the laser frequency f2 of the laser 2102 is also tuned in synchronization with the filter 2130 to maintain a fixed output frequency $f_{out}=f_{FILTER}-f2$ or $f_{out}=f2-f_{FILTER}$. This tuning of the laser 2102 to track the optical filter 2103 changes the frequency difference (f1−f2) from one desired value to another. The phase locking control module 2210 is designed to ensure the frequency difference (f1−f2) is maintained or stabilized at each of these different desired values against any drift or fluctuation between the two lasers 2101 and 2102.

FIG. 12 also shows an optical filter control 2220 for controlling the center frequency of the transmission band of the tunable optical filter 2130. A control voltage, for example, may be generated by the control 2220 to control and tune the resonance of an electro-optic optical resonator of the optical filter 2130 so as to tune the center frequency $f_{FILTER}$ of the transmission band of the filter 2130.

Figure 13:
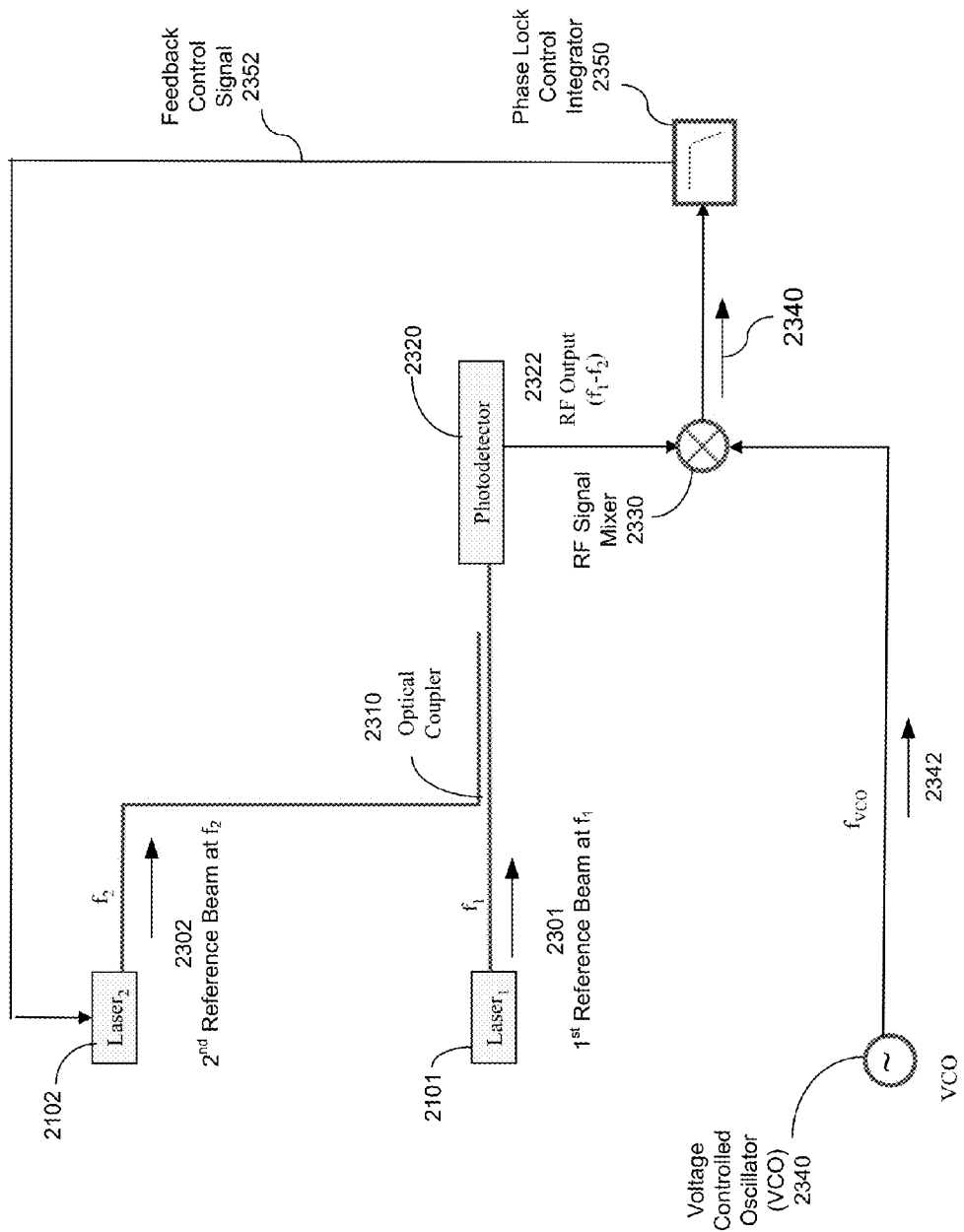
FIG. 13 illustrates one exemplary implementation of the phase locking control in FIG. 12 using a tunable voltage controlled oscillator.

FIG. 13 shows an example of the phase locking control 2210 in FIG. 12. In this example, a portion of the laser beam 2191 from the laser 2101 is split out as a first reference beam 2301 for the control 2201. Similarly, a portion of the laser beam 2192 from the laser 2102 is split out as a second reference beam 2302 for the control 2201. Such beam splitting can be achieved using optical couplers or beam splitters. A beam splitter, for example, can be placed in the optical path of each laser output in FIG. 12 to produce the respective reference beam. A beam coupler 2310 can be used to combine the two reference beams 2301 and 2302 and directs the combined beam to a photodetector 2320. The photodetector 2320 produces an RF output signal 2322 representing the beat between the two reference beams 2301 and 2302.

In addition, a voltage controlled oscillator 2340 is provided in this example for the phase locking control 2210 to produce a reference oscillation signal 2342 at a reference frequency $f_{VCO}$. An electrical signal mixer 2330 is coupled to be in communication with the optical detector 2320 to receive the detector signal 2322 and the voltage controlled oscillator 2340 to receive the reference signal 2342. The mixer 2330 is operable to mix the detector output 2322 and the reference oscillation signal 2342 to produce an error signal 2332 representing a deviation of the difference between the first laser frequency f1 and the second laser frequency f2 from the reference frequency fvco. A control circuit 2350 is provided to receive the error signal 2332 and, in response to the error signal 2332, controls one or both of the first and second lasers 2101 and 2102 to minimize the deviation so that the difference between the first laser frequency f1 and the second laser frequency f2 approaches the reference frequency fvco. In this example, a control signal 2352 is applied to the tunable laser 2102 to modify the laser frequency f2 so that the difference (f1−f2) is maintained at the reference frequency fvco. In one implementation, for example, the circuit 2350 can be an integrator that integrates the error signal to produce the control signal 2352 which controls the laser frequency f2 to nullify the output of the mixer 2330 so that fvco=f1-f2 assuming f1 is greater than f2.

Under this phase locking condition, the frequency of the receiver output signal 2160 is $$f_{out} = f_{FILTER} - f2 = (f_{FILTER} + f_{VCO}) - f1, \text{ or}$$

$$f_{out} = f2 - f_{FILTER} = f1 - (f_{FILTER} + f_{VCO})$$

when f1 is greater than f2; and $$f_{out} = f_{FILTER} - f2 = (f_{FILTER} - f_{VCO}) - f1, \text{ or}$$

$$f_{out} = f2 - f_{FILTER} = f1 - (f_{FILTER} - f_{VCO})$$

when f1 is less than f2. Hence, the frequency fvco can be tuned to make (f1-f2) to follow the value of fvco in synchronization with the tuning of the center frequency $f_{FILTER}$ of the optical filter 2130. This provides a mechanism to fix the output frequency fout at a desired signal frequency in the signal 160 for subsequent processing.

The tunable optical filter 2130 in the receivers in FIGS. 11 and 12 may be implemented in various configurations. For example, the tuning may be achieved by thermal control of the resonator whose index, dimension, or both change with temperature, mechanical control of the resonator by changing the dimension of the resonator, electrical control, or optical control. Electro-optic materials may be used to control and tune the resonance frequency of the WGM resonator by an external control signal For example, a single lithium niobate microresonator that supports whispering gallery modes is a tunable optical filter based on the electro-optic effect of the lithium niobate material and can be used as the filter 2130.

FIG. 14 shows an example of an RF device based on the receiver in FIG. 11 or 12. An antenna or circuit 1410 is provided to direct an RF signal 2120 to the receiver 2100. The receiver 2100 processes the signal 2120 to produce a receiver output signal 2160 that is either up converted or down converted in frequency to a desired carrier frequency suitable for processing by a processing circuit 1420. This design can be used in a wide range of communication devices for wired and wireless communications.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

Only a few implementations are disclosed. Variations and enhancements of the described implementations and other implementations can be made based on what is described and illustrated in this document.

What is claimed is:

1. A sensor array, comprising:
a plurality of reconfigurable sensors spatially distributed at different locations, each sensor including a movable sensor platform that adjusts or moves the sensor relative to one or more other sensors to change a spatial distribution of the sensors in the sensor array, each sensor including a sensing device that receives and detects an input signal at a respective sensor location so that different sensors at different locations receive and detect different input signals received at different locations to produce a sensor array signal based on the different received input signals at different sensors, each sensor being adjustable or reconfigurable to change one or more aspects of the sensor operation, each sensor comprising a transceiver in wireless communication with other sensors in the sensor array,
wherein the sensors are operable to collaborate with one another via wireless inter-sensor communications to reconfigure one or more aspects of the sensor array including relative positioning of two or more sensors in the sensor array.

2. The sensor array as in claim 1, wherein:
each sensor is a tunable optical sensor.

3. The sensor array as in claim 1, wherein:
each sensor is a tunable radio frequency (RF) sensor.

4. The sensor array as in claim 3, wherein:
the tunable RF sensor includes an internal photonic module that uses photonic or optical components to process light that is modulated to carry an RF signal to effectuate tuning of a frequency of a received RF signal at the tunable RF sensor.

5. The sensor array as in claim 1, wherein:
each sensor is a tunable microwave sensor.

6. The sensor array as in claim 5, wherein:
the tunable microwave sensor includes an internal photonic module that uses photonic or optical components to process light that is modulated to carry a microwave signal to effectuate tuning of a frequency of a received microwave signal at the tunable microwave sensor.

7. The sensor array as in claim 1, wherein:
each sensor is a tunable millimeter wave sensor.

8. The sensor array as in claim 7, wherein:
the tunable millimeter wave sensor includes an internal photonic module that uses photonic or optical components to process light that is modulated to carry a millimeter wave signal to effectuate tuning of a frequency of a received millimeter wave signal at the tunable millimeter wave sensor.

9. The sensor array as in claim 1, wherein:
a movable sensor platform of a sensor includes a ground vehicle, a water vessel that either floats on water or submerges in water, an airborne vehicle or a space vehicle, and is movable relative to other sensors in position to change a spatial distribution of the sensors in the array.

10. The sensor array as in claim 1, wherein:
the movable sensor platform is configured to adjust or move a position, orientation or motion of the sensor.

11. The sensor array as in claim 1, wherein:
the one or more aspects of the sensor operation of a sensor includes a frequency of a signal that is received by the sensor.

12. The sensor array as in claim 1, wherein:
each sensor includes a tunable receiver that adjusts a frequency of a received signal, and a wireless communication transceiver that provides the inter-sensor communications with other sensors.

13. The sensor array as in claim 1, wherein:
the sensors are operable to wirelessly communicate with a ground station that provides a control over an operation of the sensor array.

14. The sensor array as in claim 1, wherein:
each sensor includes an imaging sensor that captures an image of a target and different sensors capture different images of the target from different positions in the sensor array, and
each sensor further includes a wireless communication transceiver that provides the inter-sensor communications with other sensors to enable collaboration of the sensors to reconfigure one or more aspects of the sensor array in capturing images of the target including adjusting a position of one or more sensors relative to the target.

15. The sensor array as in claim 1, wherein:
each sensor includes a tunable radio frequency (RF) sensor that includes an internal photonic module that uses photonic or optical components to process light that is modulated to carry an RF signal to tune a frequency of a received RF signal.

16. The sensor array as in claim 15, wherein:
each sensor includes one or more additional sensors other than the tunable RF sensor that receives RF signals from the target object.

17. The sensor array as in claim 15, wherein:
the tunable RF sensor includes:
an input port to receive an input RF signal received from the target object,
a laser to produce a continuous-wave laser beam,
a first optical path to receive a first portion of the laser beam, and
a second optical path operable to receive a second portion of the laser beam and including an optical modulator to modulate the second portion in response to the input RF signal to produce a modulated optical beam that carries the RF input signal, a tunable optical filter to filter the modulated optical beam to select at least one spectral component in the input signal while rejecting other spectral components and to output a filtered modulated optical beam that carries the at least one selected spectral component, and a tuning control unit to tune the tunable optical filter to change a frequency of the at least one selected spectral component, and
an optical detector to combine the first portion from the first optical path and the filtered modulated optical beam from the second optical path to produce a filtered output signal comprising the at least one selected spectral component.

18. The sensor array as in claim 15, wherein:
the tunable RF sensor includes:
a first laser to produce a first continuous-wave (CW) laser beam at a first laser frequency,
an optical modulator to receive the first CW laser beam and an input RF signal from the target object and operable to modulate the first CW laser beam in response to the input RF signal to produce a modulated optical beam that carries the input RF signal,
a tunable optical filter to filter the modulated optical beam from the optical modulator to select at least one spectral component in the modulated optical signal while rejecting other spectral components and to output a filtered modulated optical beam that carries the at least one selected spectral component,
a filter control unit to tune a center frequency of the tunable optical filter to tune the at least one selected spectral component,
a second laser to produce a second CW laser beam at a second laser frequency,
an optical detector to receive both the filtered modulated optical beam from the tunable optical filter and the second CW laser beam to produce a received RF signal at a received RF frequency as output of the tunable RF receiver, and
a control unit to lock the first and second lasers in phase relative to each other and to control the first and the second lasers to tune a difference between the first and the second laser frequencies in response to the tuning of the center frequency of the tunable optical filter to maintain the output frequency of the receiver output signal at a desired fixed frequency.

19. The sensor array as in claim 1, wherein:
each sensor includes a tunable RF receiver which is tunable in frequency so that the sensor array is a tunable RF receiver array,
each sensor further includes a wireless communication transceiver that provides the inter-sensor communications with other sensors to enable collaboration of the sensors to reconfigure one or more aspects of the sensor array, and
the sensor array operates to adjust one or more tunable RF receivers in frequency or to control the movable sensor platforms of the sensors in adjusting a position of one or more sensors to dynamically reconfigure the sensor array.

20. The sensor array as in claim 19, wherein:
each tunable RF receiver includes an internal photonic module that includes photonic or optical components to process and modulate light to carry an RF signal to effectuate tuning of a frequency of a received RF signal.

\* \* \* \* \*